US009468707B2

(12) United States Patent
Pacetti et al.

(10) Patent No.: US 9,468,707 B2
(45) Date of Patent: *Oct. 18, 2016

(54) BIODEGRADABLE TRIBLOCK COPOLYMERS FOR IMPLANTABLE DEVICES

(71) Applicant: Abbott Cardiovascular Systems Inc., Santa Clara, CA (US)

(72) Inventors: Stephen D. Pacetti, San Jose, CA (US); O. Mikael Trollsas, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/752,637

(22) Filed: Jun. 26, 2015

(65) Prior Publication Data

US 2015/0374885 A1 Dec. 31, 2015

Related U.S. Application Data

(63) Continuation of application No. 14/081,287, filed on Nov. 15, 2013, now Pat. No. 9,090,745, which is a continuation of application No. 11/824,011, filed on Jun. 29, 2007, now abandoned.

(51) Int. Cl.
| | |
|---|---|
| *A61F 2/00* | (2006.01) |
| *A61F 13/00* | (2006.01) |
| *A61K 38/00* | (2006.01) |
| *A61F 2/04* | (2013.01) |
| *A61L 31/10* | (2006.01) |
| *A61L 29/04* | (2006.01) |
| *A61L 29/16* | (2006.01) |
| *A61L 31/04* | (2006.01) |
| *A61L 31/16* | (2006.01) |
| *A61K 31/436* | (2006.01) |
| *A61L 31/06* | (2006.01) |
| *C08G 81/00* | (2006.01) |

(52) U.S. Cl.
CPC .............. *A61L 31/10* (2013.01); *A61K 31/436* (2013.01); *A61L 29/041* (2013.01); *A61L 29/16* (2013.01); *A61L 31/048* (2013.01); *A61L 31/06* (2013.01); *A61L 31/16* (2013.01); *C08G 81/00* (2013.01); *A61L 2300/606* (2013.01); *A61L 2420/00* (2013.01)

(58) Field of Classification Search
None
See application file for complete search history.

(56) References Cited

U.S. PATENT DOCUMENTS

| | | |
|---|---|---|
| 4,052,988 A | 10/1977 | Doddi et al. |
| 5,085,628 A | 2/1992 | Engebretson et al. |
| 5,085,629 A | 2/1992 | Goldberg et al. |
| 5,236,444 A | 8/1993 | Muth et al. |
| 5,272,012 A | 12/1993 | Opolski |
| 5,304,121 A | 4/1994 | Sahatjian |
| 5,322,925 A | 6/1994 | Muth et al. |
| 5,342,621 A | 8/1994 | Eury et al. |
| 5,464,650 A | 11/1995 | Berg et al. |
| 5,468,253 A | 11/1995 | Bezwada et al. |
| 5,637,113 A | 6/1997 | Tartaglia et al. |
| 5,665,428 A | 9/1997 | Cha et al. |
| 5,670,161 A | 9/1997 | Healy et al. |
| 5,674,192 A | 10/1997 | Sahatjian et al. |
| 5,702,717 A | 12/1997 | Cha et al. |
| 5,702,754 A | 12/1997 | Zhong |
| 5,834,582 A | 11/1998 | Sinclair et al. |
| 5,997,517 A | 12/1999 | Whitbourne |
| 6,001,117 A | 12/1999 | Huxel et al. |
| 6,110,483 A | 8/2000 | Whitbourne et al. |
| 6,153,252 A | 11/2000 | Hossainy et al. |
| 6,224,622 B1 | 5/2001 | Kotzev |
| 6,274,164 B1 | 8/2001 | Novich |
| 6,306,176 B1 | 10/2001 | Whitbourne |
| 6,494,862 B1 | 12/2002 | Ray et al. |
| 6,503,538 B1 | 1/2003 | Chu et al. |
| 6,544,223 B1 | 4/2003 | Kokish |
| 6,544,543 B1 | 4/2003 | Buchk et al. |
| 6,656,216 B1 | 12/2003 | Hossainy |
| 6,656,506 B1 | 12/2003 | Wu et al. |
| 6,663,662 B2 | 12/2003 | Pacetti et al. |
| 6,663,880 B1 | 12/2003 | Roorda et al. |
| 6,673,154 B1 | 1/2004 | Pacetti et al. |
| 6,703,040 B2 | 3/2004 | Katsarava |
| 6,712,845 B2 | 3/2004 | Hossainy |
| 6,743,462 B1 | 6/2004 | Pacetti |

(Continued)

FOREIGN PATENT DOCUMENTS

| | | |
|---|---|---|
| CA | 2 615 243 | 7/2006 |
| EP | 0 420 541 | 4/1991 |

(Continued)

OTHER PUBLICATIONS

U.S. Appl. No. 11/888,808, filed Aug. 1, 2007, Ding.

(Continued)

*Primary Examiner* — Jeffrey T Palenik
(74) *Attorney, Agent, or Firm* — Squire Patton Boggs (US) LLP

(57) ABSTRACT

The present invention is directed to polymeric materials made of biodegradable, bioabsorbable triblock copolymers and implantable devices (e.g., drug-delivery stents) containing such polymeric materials. The polymeric materials may also contain at least one therapeutic substance. The polymeric materials are formulated so as to improve the mechanical and adhesion properties, degradation, biocompatibility and drug permeability of such materials and, thus, implantable devices formed of such materials.

22 Claims, No Drawings

(56) References Cited

U.S. PATENT DOCUMENTS

| | | |
|---|---|---|
| 6,747,121 B2 | 6/2004 | Gogolewski et al. |
| 6,753,071 B1 | 6/2004 | Pacetti |
| 6,758,859 B1 | 7/2004 | Dang et al. |
| 6,780,424 B2 | 8/2004 | Claude |
| 6,790,228 B2 | 9/2004 | Hossainy |
| 6,818,063 B1 | 11/2004 | Kerrigan |
| 6,824,559 B2 | 11/2004 | Michal |
| 6,916,788 B2 | 7/2005 | Seo et al. |
| 6,926,919 B1 | 8/2005 | Hossainy et al. |
| 6,972,054 B2 | 12/2005 | Kerrigan |
| 7,005,137 B1 | 2/2006 | Hossainy et al. |
| 7,022,334 B1 | 4/2006 | Ding |
| 7,056,591 B1 | 6/2006 | Pacetti et al. |
| 7,060,093 B2 | 6/2006 | Dang |
| 7,074,276 B1 | 7/2006 | Van Sciver et al. |
| 7,115,300 B1 | 10/2006 | Hossainy et al. |
| 7,135,038 B1 | 11/2006 | Limon |
| 7,153,520 B2 | 12/2006 | Seo et al. |
| 7,160,592 B2 | 1/2007 | Rypacek et al. |
| 7,166,680 B2 | 1/2007 | Desnoyer |
| 7,169,178 B1 | 1/2007 | Santos et al. |
| 7,175,874 B1 | 2/2007 | Pacetti |
| 7,201,935 B1 | 4/2007 | Claude et al. |
| 7,202,325 B2 | 4/2007 | Hossainy |
| 7,217,426 B1 | 5/2007 | Hossainy |
| 7,232,490 B1 | 6/2007 | Hossainy |
| 7,232,573 B1 | 6/2007 | Ding |
| 7,244,443 B2 | 7/2007 | Pacetti |
| 7,247,313 B2 | 7/2007 | Roorda et al. |
| 7,255,891 B1 | 8/2007 | Pacetti |
| 7,261,946 B2 | 8/2007 | Claude |
| 7,288,609 B1 | 10/2007 | Pacetti |
| 7,294,329 B1 | 11/2007 | Ding |
| 7,311,980 B1 | 12/2007 | Hossainy et al. |
| 7,323,209 B1 | 1/2008 | Esbeck et al. |
| 7,329,413 B1 | 2/2008 | Pacetti |
| 7,335,265 B1 | 2/2008 | Hossainy |
| 7,335,391 B1 | 2/2008 | Pacetti |
| 7,354,480 B1 | 4/2008 | Kokish et al. |
| 7,390,524 B1 | 6/2008 | Chen |
| 7,396,539 B1 | 7/2008 | Hossainy et al. |
| 7,431,959 B1 | 10/2008 | Dehnad |
| 7,435,788 B2 | 10/2008 | Pacetti |
| 7,481,835 B1 | 1/2009 | Pacetti et al. |
| 7,494,665 B1 | 2/2009 | Ding et al. |
| 7,504,125 B1 | 3/2009 | Pacetti et al. |
| 7,537,607 B2 | 5/2009 | Gerberding |
| 7,563,454 B1 | 7/2009 | Pacetti |
| 7,604,818 B2 | 10/2009 | Pacetti |
| 7,628,859 B1 | 12/2009 | Hossainy et al. |
| 7,632,307 B2 | 12/2009 | Pacetti et al. |
| 7,648,727 B2 | 1/2010 | Hossainy et al. |
| 7,758,880 B2 | 7/2010 | Hossainy |
| 7,785,512 B1 | 8/2010 | Pathak |
| 7,850,643 B1 | 12/2010 | Pacetti |
| 7,875,283 B2 | 1/2011 | Hossainy et al. |
| 7,959,659 B2 | 6/2011 | Ding |
| 8,007,775 B2 | 8/2011 | Hossainy et al. |
| 8,110,211 B2 | 2/2012 | Pacetti et al. |
| 8,192,752 B2 | 6/2012 | Tang et al. |
| 8,293,890 B2 | 10/2012 | Hossainy et al. |
| 8,309,112 B2 | 11/2012 | Galuser et al. |
| 8,357,391 B2 | 1/2013 | Pacetti et al. |
| 8,506,617 B1 | 8/2013 | Michal et al. |
| 8,546,519 B2 | 10/2013 | Selifonov et al. |
| 8,642,062 B2 | 2/2014 | Trollsas et al. |
| 8,685,431 B2 | 4/2014 | Pacetti |
| 9,090,745 B2 * | 7/2015 | Pacetti ............... A61L 29/041 |
| 2001/0007083 A1 | 7/2001 | Roorda |
| 2003/0072868 A1 | 4/2003 | Harish et al. |
| 2003/0073961 A1 | 4/2003 | Happ |
| 2003/0082368 A1 | 5/2003 | Reuter et al. |
| 2003/0104028 A1 | 6/2003 | Hossainy et al. |
| 2003/0105518 A1 | 6/2003 | Dutta |
| 2003/0139567 A1 | 7/2003 | Kim et al. |
| 2003/0158517 A1 | 8/2003 | Kokish |
| 2003/0190406 A1 | 10/2003 | Hossainy |
| 2003/0216307 A1 | 11/2003 | Kohn et al. |
| 2004/0001872 A1 | 1/2004 | Shih et al. |
| 2004/0047980 A1 | 3/2004 | Pacetti |
| 2004/0052858 A1 | 3/2004 | Wu et al. |
| 2004/0054104 A1 | 3/2004 | Pacetti |
| 2004/0060508 A1 | 4/2004 | Pacetti |
| 2004/0062853 A1 | 4/2004 | Pacetti et al. |
| 2004/0063805 A1 | 4/2004 | Hossainy |
| 2004/0071861 A1 | 4/2004 | Mandrusov |
| 2004/0072922 A1 | 4/2004 | Hossainy |
| 2004/0073298 A1 | 4/2004 | Hossainy |
| 2004/0086542 A1 | 5/2004 | Hossainy |
| 2004/0106987 A1 | 6/2004 | Palasis et al. |
| 2004/0148002 A1 | 7/2004 | Cheng et al. |
| 2004/0162609 A1 | 8/2004 | Hossainy et al. |
| 2004/0180132 A1 | 9/2004 | Pacetti |
| 2004/0191405 A1 | 9/2004 | Kerrigan |
| 2004/0199241 A1 | 10/2004 | Gravett et al. |
| 2004/0253203 A1 | 12/2004 | Hossainy et al. |
| 2005/0021127 A1 | 1/2005 | Kawula |
| 2005/0025799 A1 | 2/2005 | Hossainy |
| 2005/0074544 A1 | 4/2005 | Pacetti et al. |
| 2005/0112170 A1 | 5/2005 | Hossainy et al. |
| 2005/0112172 A1 | 5/2005 | Pacetti |
| 2005/0118344 A1 | 6/2005 | Pacetti |
| 2005/0214339 A1 | 9/2005 | Tang et al. |
| 2005/0226991 A1 | 10/2005 | Hossainy et al. |
| 2005/0233062 A1 | 10/2005 | Hossainy et al. |
| 2005/0265960 A1 | 12/2005 | Pacetti et al. |
| 2005/0271700 A1 | 12/2005 | Desnoyer et al. |
| 2005/0277577 A1 | 12/2005 | Hunter et al. |
| 2005/0287184 A1 | 12/2005 | Hossainy et al. |
| 2006/0002968 A1 | 1/2006 | Stewart et al. |
| 2006/0034888 A1 | 2/2006 | Pacetti et al. |
| 2006/0035854 A1 | 2/2006 | Goldstein et al. |
| 2006/0041102 A1 | 2/2006 | Hossainy et al. |
| 2006/0047095 A1 | 3/2006 | Pacettie et al. |
| 2006/0062821 A1 | 3/2006 | Simhambhatla et al. |
| 2006/0088571 A1 | 4/2006 | Chen et al. |
| 2006/0089485 A1 | 4/2006 | DesNoyer et al. |
| 2006/0093771 A1 | 5/2006 | Rypacek et al. |
| 2006/0095122 A1 | 5/2006 | Pacetti |
| 2006/0115449 A1 | 6/2006 | Pacetti |
| 2006/0171985 A1 | 8/2006 | Richard et al. |
| 2006/0246108 A1 | 11/2006 | Pacetti et al. |
| 2007/0026043 A1 | 2/2007 | Guan et al. |
| 2007/0032853 A1 | 2/2007 | Hossainy et al. |
| 2007/0117752 A1 | 5/2007 | Larsen et al. |
| 2007/0134305 A1 | 6/2007 | Ziberman |
| 2007/0141112 A1 | 6/2007 | Falotico et al. |
| 2007/0149640 A1 | 6/2007 | Andjelic et al. |
| 2007/0155906 A1 | 7/2007 | Hissink et al. |
| 2007/0178136 A1 | 8/2007 | Arney et al. |
| 2007/0264307 A1 | 11/2007 | Chen et al. |
| 2008/0008735 A1 | 1/2008 | Diener |
| 2008/0008739 A1 | 1/2008 | Hossainy et al. |
| 2008/0091262 A1 | 4/2008 | Gale et al. |
| 2008/0107704 A1 | 5/2008 | Guo |
| 2008/0147175 A1 | 6/2008 | Krivoruchko et al. |
| 2008/0248098 A1 | 10/2008 | Jin et al. |
| 2009/0047322 A1 | 2/2009 | Vange et al. |
| 2009/0088828 A1 | 4/2009 | Shalev et al. |
| 2009/0104241 A1 | 4/2009 | Pacetti |
| 2009/0110713 A1 | 4/2009 | Lim et al. |
| 2009/0111787 A1 | 4/2009 | Lim et al. |
| 2009/0263457 A1 | 10/2009 | Trollsas et al. |
| 2009/0285873 A1 | 11/2009 | Lim et al. |
| 2009/0291111 A1 | 11/2009 | Lim et al. |
| 2009/0297584 A1 | 12/2009 | Lim et al. |
| 2010/0063585 A1 | 3/2010 | Hoffmann et al. |
| 2010/0125329 A1 | 5/2010 | Lin et al. |

(56) References Cited

U.S. PATENT DOCUMENTS

| | | |
|---|---|---|
| 2011/0275700 A1 | 11/2011 | Papisov |
| 2011/0301697 A1 | 12/2011 | Hoffmann et al. |
| 2014/0072609 A1 | 3/2014 | Pacetti et al. |

FOREIGN PATENT DOCUMENTS

| | | |
|---|---|---|
| EP | 0 761 712 | 3/1997 |
| EP | 0 947 205 | 10/1999 |
| EP | 1 112 724 | 7/2001 |
| EP | 1 121 943 | 8/2001 |
| EP | 1 440 698 | 7/2004 |
| EP | 1 764 118 | 3/2007 |
| EP | 1 891 993 | 2/2008 |
| EP | 1 932 551 | 6/2008 |
| JP | 2003-205059 | 9/1991 |
| JP | 7-163654 | 6/1995 |
| JP | 2002-516910 | 6/2002 |
| JP | 2002-525404 | 8/2002 |
| JP | 2003/532489 T | 11/2003 |
| JP | 2004-505063 | 2/2004 |
| JP | 2004-525194 | 8/2004 |
| JP | 2005-516736 | 6/2005 |
| JP | 2005-519654 | 7/2005 |
| JP | 2005-230211 | 9/2005 |
| JP | 2006-512945 | 4/2006 |
| JP | 2007/520260 | 7/2007 |
| JP | 2007-190369 | 8/2007 |
| JP | 2007-521069 | 8/2007 |
| JP | 2007-522274 | 8/2007 |
| JP | 2007-532640 | 11/2007 |
| JP | 2008-508395 | 3/2008 |
| JP | 2008-500116 | 10/2008 |
| JP | 9-511666 T | 3/2009 |
| JP | 9-511741 T | 3/2009 |
| WO | WO 95/27481 | 10/1995 |
| WO | WO 95/28124 | 10/1995 |
| WO | WO 99/18142 | 4/1999 |
| WO | WO 00/18821 | 4/2000 |
| WO | WO 01/85061 | 11/2001 |
| WO | WO 02/09768 | 2/2002 |
| WO | WO 02/26215 | 4/2002 |
| WO | WO 03/020330 | 3/2003 |
| WO | WO 2004/050140 | 6/2004 |
| WO | WO 2004/108111 | 12/2004 |
| WO | WO 2005/000939 | 1/2005 |
| WO | WO 2005/011770 | 2/2005 |
| WO | WO 2005/051449 | 6/2005 |
| WO | WO 2005/053571 | 6/2005 |
| WO | WO 2005/068533 | 7/2005 |
| WO | WO 2005/110425 | 11/2005 |
| WO | WO 2005/115493 | 12/2005 |
| WO | WO 2006/026201 | 3/2006 |
| WO | WO 2006/047378 | 5/2006 |
| WO | WO 2006/065685 | 6/2006 |
| WO | WO 2006/071860 | 7/2006 |
| WO | WO 2006/074391 | 7/2006 |
| WO | WO 2006/083904 | 8/2006 |
| WO | WO 2007/009919 | 1/2007 |
| WO | WO 2007/058190 | 5/2007 |
| WO | WO 2007/101443 | 9/2007 |
| WO | WO 2007/121019 | 10/2007 |
| WO | WO 2007/139931 | 12/2007 |
| WO | WO 2008/003298 | 1/2008 |
| WO | WO 2008/058660 | 5/2008 |
| WO | WO 2008/121508 | 10/2008 |
| WO | WO 2009/005909 | 1/2009 |
| WO | WO 2009/036083 | 3/2009 |
| WO | WO 2009/055426 | 4/2009 |
| WO | WO 2009/058666 | 5/2009 |
| WO | WO 2009/058694 | 5/2009 |
| WO | WO 2009/129503 | 10/2009 |
| WO | WO 2009/148926 | 12/2009 |
| WO | WO 2010/021883 | 2/2010 |
| WO | WO 2010/147603 | 12/2010 |

OTHER PUBLICATIONS

Agnihotri et al. "Osteopontin, a Novel Substrate for Matrix Metalloproteinase-3 (Stromelysin-1) and Matrix Metalloproteinase-7 (Matrilysin)" Journal of Biological Chemistry, vol. 276, No. 30, 2001, pp. 28261-28267.

Boolchand, "The Maximum in Glass Transition Temperature ($T_g$) near $x = \frac{1}{3}$ in $Ge_xSe_{1-x}$ Glasses," Asian Journal of Physics, 2000, vol. 9 No. 3, pp. 709-721.

Buchholz, B., "Analysis and characterization of resorbable DL-lactide-trimethylene carbonate copolyesters," Journal of Materials Science: Materials in Medicine, vol. 4, 1993, pp. 381-388.

Cai et al., "Synthesis and Characterization of Polycaprolactone (B)-Poly(lactide-co-glycolide) (A) ABA Block Copolymer", Polym. Adv. Technol., vol. 11, pp. 159-166 (2000).

Chu et al., Ed. "Wound Closure Biomaterials and Devices; Chemical structure and Manufacturing Processes," CRC Press, 1997, pp. 65-106.

Ettmayer et al. "Lessons learned from Market and investifational Prodrugs," Journal of Medicinal of Chemistry, vol. 47, 2004, pp. 2394.

Examination report dated Aug. 5, 2010, for European patent application No. 08 769 646.4, 5 pp.

Farrar et al. "Hydrolytic degradation of polyglyconate B: the relationship between degradation time, strength and molecular weight," Biomaterials, vol. 23, 2002, pp. 3905-3912.

Forrest, J.A. et al. "Effect of Free Surfaces on the Glass Transition Temperature of Thin Polymer Films," Physical Review Letters, vol. 77, No. 10, pp. 2002-2006.

Forrest, J.A. et al. "Interface and chain confinement effects on the glass transition temperature of thin olymer films," Physical Review E, 1997, vol. 56, No. 5, pp. 5705-5716.

Gabbott Ed. Principles and Applications of Thermal Analysis "Chapter 2: Fast Scanning DSC," 10 pp.

Gruberg, Luis M.D. "Drug-Eluting Stents at a Crossroads: Stent Thrombosis and Safety," Medscap Cardiology, 2015, 7 pp.

Hanefeld et al. "Coating of Poly(p-xylylene) by PLA-PEO_PLA Triblock Copolymers with Excellent Polymer-Polymer Adhesion for Stent Applications," Biomacromolecules, Jun. 10, 2006, [online], doi: 10.1021/bm050642k, Retrieved from the internet: <URL: http://pubs.-acs.-org/doi/abs/10.1021/bm050642I> (vol. 7, No. 7, pp. 2086-2090).

Harper, "Drug Latentiation", Prog. Drug. Res., 4: pp. 221-294 (1962).

Hefferman et al. "Polyketal Nanoparticles: A New pH-Sensitive Biodegradable Drug Delivery Vehicle," Bioconjugate Chem. vol. 16, 2005, pp. 1340-1342.

Hill, et al "Dynamic mechanical studies of hydrolytic degradation in isotropic and oriented Maxon B," Biomaterials, vol. 27, 2006, pp. 3168-3177.

Iannelli et al. Selective Microwave-Accelerated Synthesis and Polymerization of Chiral Methacrylamide Directly from Methacyrylic Acid and (R)-1Phenyl-Ethylamine, 2004.

Inoue, Akihisa et al. "Zr—Al—Ni Amorphous Alloys with High Glass Transition Temperature and Significant Supercooled Liquid Region," Materials Transactions, JIM, vol. 31, No. 3, 1990, pp. 177-183.

International Search Report for PCT/US2008/064585, mailed Sep. 1, 2009, 9 pgs.

Jeong, Byeongmoon et al. "Drug release from biodegradable injectable thermosensitive hydrogel of PEG-PLGA-PEG triblock copolymers," Journal of Controlled Release, 2000, vol. 63, pp. 155-163. Abstract.

Jie et al, "Preparation, Characterization and Biodegradable Characteristics of Poly (1,3-trimethylene carbonate-co-glycolide)" Polymer International, vol. 41, 1996, pp. 369-375.

Journal of Controlled Release, 2001, vol. 72, No. 1-3, pp. 203-215.

Joziasse et al., "Rubber toughened linear and star-shaped poly(d,l-lactide-co-glycolide): synthesis, properties and in vitro degradation ", Polymer, vol. 39, No. 2, pp. 467-473 (1998).

(56) References Cited

OTHER PUBLICATIONS

Kricheldorf et al., "A-B-A-Triblock and multiblock copolyesters prepared from ε-caprolactone, glycolide and L-lactide by means of bismuth subsalicylate", Polymer, vol. 46, pp. 3248-3256 (2005).

Lee et al. "Communications: Polyketal Microparticles: A new Delivery Vehicle for Superoxide Dismutase," Bioconjugate Chem., vol. 18, 2007, pp. 4-7.

Lee et al., "Synthesis and Gelation of DOPA-Modified Poly(ethylene glycol) Hydrogels", Biomacromolecules 3, pp. 1038-1047 (2002).

Martin et al, "Enhancing the biological activity of immobilized osteopontin using a type-1 collagen affinity coating", Wiley Periodicals, Inc. pp. 10-19 (2004).

Metz et al. "In vivo and in vitro degradation of monofilament absorbable sutures, PDS and Maxon," Biomaterials, vol. 11, 1990, pp. 41-45.

Nair et al. "Polymers as Biomaterials for Tissue Engineering and Controlled Drug Delivery," Adv. Biochem/Engin/Biotechnol, vol. 102, 2006, pp. 47-90.

Noorsal et al. "Degradation and Drug-Release Studies of a Poly(glycolide-co-trimethylene carbonate) Copolymer (Maxon)," Journal of Applied Polymer Science, vol. 95, 2005, pp. 475-486.

Notice of Reasons for Rejection dated Mar. 26, 2013, for Japanese Patent Application No. P2010-514912, 4 pp.

Notice of Reasons for Rejection from JPO for P2010-514912, dispatched Jan. 7, 2014, with the translation, 6 pgs.

Ravel, Ankur, "Novel Biodegradable polymeric Matrix Coated Cardiovascular Stent for Controlled Drug Delivery," Trends Biomater. Artif. Organs, vol. 20, No. 2, 2007, pp. 131-141.

Richard et al. "Evaluation of Acrylate-Based Block Copolymers Prepared by Atom Transfer Radical Polymerization as Matrices for Paclitaxel Delivery from Coronary Stents," Biomacromolecules, 2005, vol. 6, No. 6, pp. 3410-3418.

Roche, Editor, "Design of Bipharmaceutical Properties through Prodrugs and Analogs", book, 4 pgs. (1997).

Sakurai et al. "Glass transition temperature of chitosan and miscibility of chitosan/poly(N-vinyl pyrrolidone) blends," Polymer, 2000, vol. 41, pp. 7051-7056.

Shalaby ed. Biomedical Polymers—Chapter 1: Synthetic Absorbable Polyesters, pp. 1-33.

Shin et al. "Attachement, proliferation, and migration of marrow strmal osteoblasts cultured on biomimetic hydrogels modified with an osteopontin-derived peptide," Biomaterials, vol. 25, 2004, pp. 895-906.

Sinkula et al., "Rationale for Design of Biologically Reversible Drug Derivatives: Prodrugs", J. of Pharmaceutical Sciences vol. 64, No. 2, pp. 181-210 (1975).

Sipos et al, "Controlled Delivery of Paclitaxel from Stent Coatings Using Poly(hydroxystyren-b-isobutylene-b-hydroxystyrene) isobutylene-b-hydroxystyrene) and its Acetylated Derivative," Biomacromolecules, 2005, vol. 6, No. 5, pp. 2570-2582.

Spagnuolo et al., "Gas1 is induced by VE-cadherin and vascular endothelial growth factor and inhibits endothelial cell apoptosis", Blood, vol. 103, No. 8, pp. 3005-3012 (2004).

Stella et al., "Prodrugs Do They Have Advantages in Clinical Practice?", Drugs 29: pp. 455-473 (1985).

Translation of the Notice of Reasons for Rejection dated Mar. 26, 2013, for Japanese Patent Application No. P2010-514912, 4 pp.

Völkel et al., "Targeting of immunoliposomes to endothelial cells using a single-chain Fv fragment directed against human endoglin (CD105)", Biochimica et Biophysica Acta 1663, pp. 158-166 (2004).

Zhou et al. "Syntheses and Characterization of Poly(cyclohexyl vinyl ether-*stat*-vinyl alcohol)-*b*-polyisobutylene-*b*-polysobutylene-*b*-poly(cyclohexyl vinyl ether-*stat*-vinyl alcohol) Triblock Copolymers and Their Application as Coatings to Deliver Paclitaxel from Coronary Stents," Macromolecules, 2005, vol. 38, No. 20, pp. 8183-8191.

Bezwada "Monocryl Suture, a new ultra-pliable absorbable monofilament suture", Biomaterials vol. 16, No. 15 pp. 1141-1148 (1995).

Zentner et al., Biodegradable block copolymers for delivery of proteins and water-insoluble drugs (2001) *Journal of Controlled Release* 72:203-215.

\* cited by examiner

```
                       SEQUENCE LISTING

<160> NUMBER OF SEQ ID NOS: 1

<210> SEQ ID NO 1
<211> LENGTH: 13
<212> TYPE: PRT
<213> ORGANISM: Rattus sp.

<400> SEQUENCE: 1

Asp Val Asp Val Pro Asp Gly Asp Ser Leu Ala Tyr Gly
1               5                   10
```

BIODEGRADABLE TRIBLOCK COPOLYMERS FOR IMPLANTABLE DEVICES

CROSS-REFERENCE TO RELATED APPLICATION

This application is a continuation of U.S. patent application Ser. No. 14/081,287, filed on Nov. 15, 2013, published as United States Patent Application Publication No. US 2014-0072609 A1 on Mar. 13, 2014, and issued as U.S. Pat. No. 9,090,745 B2 on Jul. 28, 2015, which is a continuation of U.S. patent application Ser. No. 11/824,011, filed on Jun. 29, 2007, and published as United States Patent Application Publication No. US 2009/0004243 A1 on Jan. 1, 2009; and both of which applications are incorporated herein by reference.

BACKGROUND

1. Field of the Invention

The present invention is directed to polymeric materials made of biodegradable, bioabsorbable triblock copolymers and implantable devices (e.g., drug-delivery stents) containing such polymeric materials.

2. Description of the State of the Art

Angioplasty is a well-known procedure for treating heart disease. A problem associated with angioplasty includes formation of intimal flaps or torn arterial linings which can collapse and occlude the conduit after the balloon is deflated. Moreover, thrombosis and restenosis of the artery may develop over several months after angioplasty, which may require another angioplasty procedure or a surgical by-pass operation. "Stenosis" refers to a narrowing or constriction of the diameter of a bodily passage or orifice, and "restenosis" refers to the reoccurrence of stenosis in a blood vessel or heart valve after it has been treated (as by balloon angioplasty, stenting, or valvuloplasty) with apparent success.

Stents are often used in the treatment of atherosclerotic stenoses in blood vessels. To reduce the partial or total occlusion of the artery by the collapse of arterial lining and to reduce the chance of thrombosis and restenosis following angioplasty in the vascular system, a stent may be implanted in the lumen to reinforce body vessels and maintain the vascular patency. A "lumen" refers to a cavity of a tubular organ such as a blood vessel. As a mechanical intervention, stents act as scaffoldings, functioning to physically hold open and, if desired, to expand the wall of a passageway, e.g., a blood vessel, urinary tract or bile duct.

Stents are also used as a vehicle for providing biological therapy. Biological therapy can be achieved by medicating the stents. Medicated stents provide for the local administration of a therapeutic substance at the diseased site, thereby possibly avoiding side effects associated with systemic administration of such medication. One method of medicating stents involves the use of a polymeric carrier coated onto the surface of a stent, in which a therapeutic substance is impregnated in polymer.

Late stent thrombosis has emerged as a concern for drug-delivery stents. The incidence of late stent thrombosis appears to be higher with drug-delivery stents than with the corresponding bare metal stents. One potential cause of late thrombosis with drug-delivery stents is a chronic inflammatory or hypersensitivity response to the polymeric coating on the stent.

The present invention addresses late stent thrombosis and offers other advantageous features.

SUMMARY OF THE INVENTION

The present invention is directed to biodegradable polymeric materials used for implantable devices (e.g., stents) that enable the devices to perform their functions more effectively and avoid adverse effects. The polymeric materials are configured to completely or substantially completely erode after the devices accomplish their intended functions (e.g., maintaining vascular patency and locally delivering drugs), thereby avoiding adverse effects such as late stent thrombosis. Other advantages of the biodegradable polymeric materials include, among others, good mechanical properties (e.g., strength, rigidity, toughness and flexibility), control of drug-release rates, and enhanced adhesion to metal surfaces.

One embodiment of the invention is directed to a composition comprising a biodegradable triblock copolymer of the structure A-B-A', wherein:
the A and A' blocks each independently are hard blocks having a $T_g$ or $T_m$ above body temperature;
the B block is a soft block having a $T_g$ less than the $T_g$ or $T_m$ of the A and A' blocks;
the A, B and A' blocks each independently have a polymer number-average molecular weight ($M_n$) from about 1 kDa to about 500 kDa; and
the A and A' blocks may be the same or different.

In another embodiment, the tensile modulus of the hard A and A' blocks independently is greater than about 1,000 MPa, and the tensile modulus of the soft B block is less than about 1,000 MPa. In yet another embodiment, the weight fraction of the A and A' blocks is from about 1% to about 99% of the triblock copolymer. In still another embodiment, the A, B and A' blocks each independently comprise a polymer comprising from one to four different types of monomer, wherein each type of monomer has from about 5 to about 5,000 monomer units.

In a further embodiment of the ABA' triblock copolymers:
the A and A' blocks each independently comprise a polymer selected from the group consisting of poly(L-lactide) (PLLA), poly(D,L-lactide), poly(glycolide) (PGA), poly(GA-co-D,L-lactide), poly(GA-co-L-lactide), and any variations in the arrangement of the monomers thereof; and
the B block comprises a polymer selected from the group consisting of poly(caprolactone) (PCL), poly(CL-co-GA), poly(trimethylene carbonate) (PTMC), poly(TMC-co-GA), poly(TMC-co-D,L-lactide), poly(TMC-co-L-lactide), poly(TMC-co-CL), poly(TMC-co-D,L-lactide-co-GA), poly(TMC-co-CL-co-GA), poly(dioxanone), poly(TMC-co-dioxanone), poly(dioxanone-co-CL), poly(dioxanone-co-D,L-lactide), poly(dioxanone-co-L-lactide), poly(dioxanone-co-GA), poly(dioxanone-co-D,L-lactide-co-GA), polyketals, and any variations in the arrangement of the monomers thereof.

According to an embodiment, the polyketal polymer of the B block has the structure

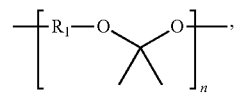

wherein $R_1$ is a poly(caprolactone) diol or a $C_2$-$C_{24}$ diol of the structure, —O—$R_2$—, that contains an optionally substituted aliphatic, heteroaliphatic, cycloaliphatic, heterocycloaliphatic, aromatic or heteroaromatic group, or a combination thereof, and n is an integer from about 5 to about 5,000.

In yet another embodiment, at least one dihydroxyaryl group is conjugated to the polymer ends of the triblock copolymer.

In still another embodiment, the composition of the invention further comprises at least one biocompatible moiety.

In a further embodiment, the composition further comprises at least one additional biologically absorbable polymer.

In some embodiments, the composition further comprises at least one biologically active agent. In an embodiment, the at least one biologically active agent is selected from the group consisting of antiproliferative, antineoplastic, anti-inflammatory, antiplatelet, anticoagulant, antifibrin, antithrombin, antimitotic, antibiotic, antiallergic and antioxidant substances.

According to another embodiment, the at least one biologically active agent is selected from the group consisting of paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, prodrugs thereof, co-drugs thereof, and a combination thereof.

Other embodiments of the invention are directed to a coating comprising any combination of embodiments of the inventive composition.

Yet other embodiments of the invention are directed to an implantable device formed of a material comprising any combination of embodiments of the inventive composition. In an embodiment, the material comprises any combination of embodiments of the inventive coating, which is disposed over the implantable device. In another embodiment, the implantable device is a stent, graft, stent-graft, catheter, lead, electrode, clip, shunt, closure device, or valve.

Still other embodiments of the invention are directed to a method of preparing any combination of embodiments of the inventive composition, e.g., via ring-opening polymerization of the corresponding monomers of the A, B and A' blocks.

Further embodiments of the invention are directed to a method of fabricating an implantable device. In one embodiment, the method comprises forming the implantable device of a material comprising any combination of embodiments of the inventive composition. In another embodiment, the method comprises depositing any combination of embodiments of the inventive coating over at least a portion of the implantable device. In some embodiments, the implantable device is a stent, graft, stent-graft, catheter, lead, electrode, clip, shunt, closure device, or valve.

Still further embodiments of the invention are directed to a method of treating or preventing a condition or disorder in a patient, comprising implanting in the patient any combination of embodiments of the inventive implantable device. In an embodiment, the condition or disorder is selected from the group consisting of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, bile duct obstruction, ureter obstruction and tumor obstruction.

Various embodiments of the invention are described in further detail below.

DETAILED DESCRIPTION OF THE INVENTION

Terms and Definitions

The following definitions apply:

The terms "biologically degradable" (or "biodegradable"), "biologically erodable" (or "bioerodable"), "biologically absorbable" (or "bioabsorbable"), and "biologically resorbable" (or "bioresorbable"), in reference to polymers and coatings, are used interchangeably and refer to polymers and coatings that are capable of being completely or substantially completely degraded, dissolved, and/or eroded over time when exposed to bodily fluids such as blood and can be gradually resorbed, absorbed and/or eliminated by the body, or that can be degraded into fragments that can pass through the kidney membrane of a human (e.g., fragments having a molecular weight of about 40,000 Daltons (40 kDa) or less). The process of breaking down and eventual absorption and elimination of the polymer or coating can be caused by, e.g., hydrolysis, metabolic processes, oxidation, enzymatic processes, bulk or surface erosion, and the like. Conversely, a "biostable" polymer or coating refers to a polymer or coating that is not biodegradable.

Whenever the reference is made to "biologically degradable," "biologically erodable," "biologically absorbable," and "biologically resorbable" stent coatings or polymers forming such stent coatings, it is understood that after the process of degradation, erosion, absorption, and/or resorption has been completed or substantially completed, no coating or substantially little coating will remain on the stent. Whenever the terms "degradable," "biodegradable," or "biologically degradable" are used in this application, they are intended to broadly include biologically degradable, biologically erodable, biologically absorbable, and biologically resorbable polymers or coatings.

"Biodegradability," "bioerodability," "bioabsorbability," and "bioresorbability" are defined as inherent property of the coating or polymer forming the coating that is biologically degradable, biologically erodable, biologically absorbable, or biologically resorbable.

As used herein, "biocompatible" moieties refer to moieties that are capable of enhancing biological compatibility of the composition, material or structure containing them.

"Physiological conditions" refer to conditions to which an implant is exposed within the body of an animal (e.g., a human). Physiological conditions include, but are not limited to, human body temperature (approximately 37° C.) and an aqueous environment of physiologic ionic strength, pH and enzymes.

In the context of a blood-contacting implantable device, a "prohealing" drug or agent refers to a drug or agent that has the property that it promotes or enhances re-endothelialization of arterial lumen to promote healing of the vascular tissue.

As used herein, a "co-drug" is a drug that is administered concurrently or sequentially with another drug to achieve a particular pharmacological effect. The effect may be general or specific. The co-drug may exert an effect different from that of the other drug, or it may promote, enhance or potentiate the effect of the other drug.

As used herein, the term "prodrug" refers to an agent rendered less active by a chemical or biological moiety, which metabolizes into or undergoes in vivo hydrolysis to form a drug or an active ingredient thereof. The term "prodrug" can be used interchangeably with terms such as "proagent", "latentiated drugs", "bioreversible derivatives", and "congeners". N. J. Harper, Drug latentiation, *Prog Drug Res.*, 4: 221-294 (1962); E. B. Roche, Design of Biopharmaceutical Properties through Prodrugs and Analogs, Washington, D.C.: American Pharmaceutical Association (1977); A. A. Sinkula and S. H. Yalkowsky, Rationale for design of biologically reversible drug derivatives: prodrugs, *J. Pharm. Sci.*, 64: 181-210 (1975). Use of the term "prodrug" usually implies a covalent link between a drug and a chemical moiety, though some authors also use it to characterize some forms of salts of the active drug molecule. Although there is no strict universal definition of a prodrug itself, and the definition may vary from author to author, prodrugs can generally be defined as pharmacologically less active chemical derivatives that can be converted in vivo, enzymatically or nonenzymatically, to the active, or more active, drug molecules that exert a therapeutic, prophylactic or diagnostic effect. Sinkula and Yalkowsky, above; V. J. Stella et al., Prodrugs: Do they have advantages in clinical practice?, *Drugs*, 29: 455-473 (1985).

The terms "block copolymer" and "graft copolymer" are defined in accordance with the terminology used by the International Union of Pure and Applied Chemistry (IUPAC). "Block copolymer" refers to a copolymer containing a linear arrangement of blocks. The block is defined as a portion of a polymer molecule in which the monomer units have at least one constitutional or configurational feature absent from the adjacent portions. "Graft copolymer" refers to a polymer composed of macromolecules with one or more species of block connected to the main chain as side chains, these side chains having constitutional or configurational features that differ from those in the main chain.

The term "ABA' triblock copolymer" is defined as a block copolymer having moieties A, B and A' arranged according to the general formula $-\{[A-]_m-[B]_n-[A']_p\}-_x$, where each of "m," "n," "p" and "x" independently is a positive integer $\geq 1$. For example, each of m, n, and p independently may be $\geq 1$ and $\leq 10,000$.

The blocks of the ABA' triblock copolymer need not be linked on the ends, since the values of the integers determining the number of A, B and A' blocks are such as to ensure that the individual blocks are usually long enough to be considered polymers in their own right. Accordingly, the ABA' triblock copolymer can be named poly A-block-poly B-block-poly A' block copolymer. Blocks A, B and A' can be alternating or random.

As used herein, a material that is described as a coating "disposed over" an indicated substrate, e.g., an implantable device, refers to a coating of the material deposited directly or indirectly over at least a portion of the surface of the substrate. Direct depositing means that the coating is applied directly to the exposed surface of the substrate. Indirect depositing means that the coating is applied to an intervening layer that has been deposited directly or indirectly over the substrate.

As used herein, an "implantable device" may be any device that can be implanted in an animal. Examples of implantable devices include, but are not limited to, self-expandable stents, balloon-expandable stents, coronary stents, peripheral stents, stent-grafts, catheters, other expandable tubular devices for various bodily lumen or orifices, grafts, vascular grafts, arterio-venous grafts, bypass grafts, pacemakers and defibrillators, leads and electrodes for the preceding, artificial heart valves, anastomotic clips, arterial closure devices, patent foramen ovale closure devices, and cerebrospinal fluid shunts. The stents may be intended for any vessel in the body, including neurological, carotid, vein graft, coronary, aortic, renal, iliac, femoral, popliteal vasculature, and urethral passages. An implantable device can be designed for the localized delivery of a therapeutic agent. A medicated implantable device may be constructed by coating the device or substrate with a coating material containing a therapeutic agent. The substrate of the device may also contain a therapeutic agent. An implantable device can be fabricated with a coating containing partially or completely a biodegradable/bioabsorbable/bioerodable polymer, a biostable polymer, or a combination thereof. An implantable device itself can also be fabricated partially or completely from a biodegradable/bioabsorbable/bioerodable polymer, a biostable polymer, or a combination thereof.

The "glass transition temperature", $T_g$, is the temperature at which the amorphous domains of a polymer change from a brittle, glassy, vitreous state to a solid deformable, ductile or rubbery state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised, the actual molecular volume in the sample remains constant, and so a higher coefficient of expansion points to an increase in free volume associated with the system and therefore increased freedom for the molecules to move. The increasing heat capacity corresponds to an increase in heat dissipation through movement. The $T_g$ of a given polymer can be dependent on the heating rate and can be influenced by the thermal history of the polymer. Furthermore, the chemical structure of the polymer heavily influences the glass transition by affecting chain mobility.

The "melting temperature", $T_m$, is the temperature at which the crystalline domains of a polymer lose their short- and long-term order, changing from a regular, ordered structure of chain packing to that of a disordered structure, resembling an amorphous polymer. The disappearance of the polymer crystalline phase is accompanied by changes in physical properties of the polymer. The material becomes a viscous solid, with discontinuous changes in the density, refractive index, heat capacity, transparency, and other properties. The $T_m$ of a given polymer occurs over a finite temperature range. The breadth of the transition is dependent on the size and perfection of the polymer crystallites, as well as their homogeneity and purity. By thermal analytical techniques, the $T_m$ of a semi-crystalline polymer is an endothermic transition when the heating rate is positive. The ability of the polymer chains to pack into an ordered, repeating structure is heavily influenced by the chemical structure of the polymer.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus. A material with a relatively high modulus tends to be stiff or rigid. Conversely, a material with a relatively low modulus tends to be flexible. The modulus of a material depends on the molecular composition and structure, temperature of the material, amount of deformation, and the strain rate or rate of deformation. For example, below its $T_g$, a polymer tends to be brittle with a high modulus. As the temperature of a polymer is increased from below to above its $T_g$, its modulus decreases.

"Strain" refers to the amount of elongation or compression that occurs in a material at a given stress or load.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

The terms "alkyl" and "aliphatic group" refer to an optionally substituted, straight-chain or branched, saturated or unsaturated hydrocarbon moiety that may contain one or more heteroatoms selected from O, S, and N. If unsaturated, the alkyl or aliphatic group may contain one or more double bonds and/or one or more triple bonds. The alkyl or aliphatic group may be monovalent (i.e., —R) or divalent (i.e., —R—) in terms of its attachment to the rest of the compound. Examples of alkyl and aliphatic groups include, but are not limited to, methyl, ethyl, ethylenyl, ethynyl, n-propyl, isopropyl, propenyl, propynyl, n-butyl, isobutyl, sec-butyl, tertiary-butyl, butenyl, butyryl, n-pentyl, isopentyl, pentenyl, and pentynyl.

The terms "heteroalkyl" and "heteroaliphatic group" refer to an alkyl or aliphatic group that contains at least one heteroatom selected from O, S and N, in the main portion and/or the branch(es) of the hydrocarbon moiety. Examples of heteroalkyl and heteroaliphatic groups include, but are not limited to, alcohols, ethers, oxo compounds, ketones, aldehydes, esters, carbonates, thioesters, thiols, sulfides, sulfoxides, sulfones, sulfonamides, amino compounds, amines, nitriles, N-oxides, imines, oximes, amides, carbamates, ureas, and thioureas.

The terms "cycloalkyl" and "cycloaliphatic group" refer to an optionally substituted, saturated or unsaturated, mono- or polycyclic hydrocarbon moiety that may contain one or more heteroatoms selected from O, S, and N. If unsaturated, the cycloalkyl or cycloaliphatic group may contain one or more double bonds and/or one or more triple bonds in and/or off of one or more rings of the cyclic moiety. The cycloalkyl or cycloaliphatic group may be monovalent (i.e., -Cyc) or divalent (i.e., -Cyc-) in terms of its attachment to the rest of the compound. Examples of cycloalkyl and cycloaliphatic groups include, but are not limited to, cyclopropyl, cyclobutyl, cyclopentyl, cyclopentenyl, cyclohexyl, cyclohexenyl, decahydronaphthyl, and octahydroindyl.

The terms "heterocycloalkyl" and "heterocycloaliphatic group" refer to a cycloalkyl or cycloaliphatic group in which at least one ring in the cyclic moiety contains one or more heteroatoms selected from O, S, and N. Examples of heterocycloalkyl and heterocycloaliphatic groups include, but are not limited to, aziridinyl, oxiranyl, oxolanyl, thiolanyl, pyrrolidinyl, 3-pyrrolinyl, dioxalanyl, 1,3-dithiolanyl, oxazolidinyl, imidazolidinyl, oxanyl, piperidinyl, piperazinyl, 1,3-dioxanyl, 1,4-dioxanyl, morpholinyl, octahydroindolyl, octahydroisoindolyl, octahydrobenzofuryl, octahydrobenzothiophene, octahydrochromenyl, and decahydroquinolinyl.

The terms "aryl" and "aromatic group" refer to an optionally substituted mono- or polycyclic aromatic moiety in which at least one ring in the moiety is aromatic. The ring(s) in the moiety may be carbocyclic or may contain one or more heteroatoms selected from O, S, and N. The ring(s) in the moiety may be aromatic or non-aromatic (saturated or unsaturated), but at least one ring in the moiety is aromatic. An aryl or aromatic group may be monovalent (i.e., —Ar) or divalent (i.e., —Ar—) in terms of its attachment to the rest of the compound. Examples of aryl and aromatic groups include, but are not limited to, phenyl, indolinyl, isoindolinyl, 2,3-dihydrobenzofuryl, 2,3-dihydrobenzothiophene, chromanyl, 1,2,3,4-tetrahydroquinolinyl, 1,2,3,4-tetrahydroisoquinolinyl, naphthyl, indenyl, and indanyl.

The terms "heteroaryl" and "heteroaromatic group" refer to an aryl or aromatic group in which at least one ring (aromatic or non-aromatic) in the aromatic moiety contains one or more heteroatoms selected from O, S, and N. Examples of heteroaryl and heteroaromatic groups include, but are not limited to, pyrrolyl, pyrazolyl, imidazolyl, furyl, isoxazolyl, oxazolyl, thiophenyl, thiazolyl, isothiazolyl, triazolyl, oxadiazolyl, thiadiazolyl, tetrazolyl, pyridyl, pyridazinyl, pyrimidinyl, pyrazinyl, 1,3,5-triazinyl, indolyl, isoindolyl, benzofuranyl, benzothiophenyl, indazolyl, benzimidazolyl, benzothiazolyl, [1,7]naphthyridinyl, chromenyl, quinolinyl, isoquinolinyl, cinnolinyl, quinazolinyl, quinoxalinyl, phthalazinyl, purinyl, pyridazinyl, quinolinyl, imidazo[4,5-c]pyridinyl, pyrido[2,3-d]pyrimidinyl, pyrimido[3,2-c]pyrimidinyl, and pyrrolo[2,3-d]pyrimidinyl.

The alkyl, aliphatic, heteroalkyl, heteroaliphatic, cycloalkyl, cycloaliphatic, heterocycloalkyl, heterocycloaliphatic, aryl, aromatic, heteroaryl and heteroaromatic groups may be substituted or unsubstituted. If substituted, they may contain from 1 to 5 substituents. The substituents include, but are not limited to: optionally substituted carbon-containing groups, e.g., alkyl, cycloalkyl and aryl (e.g., benzyl); halogen atoms (i.e., F, Cl, Br and I) and optionally substituted halogen-containing groups, e.g., haloalkyl (e.g., trifluoromethyl); optionally substituted oxygen-containing groups, e.g., oxo, alcohols (e.g., hydroxyl, hydroxyalkyl, aryl(hydroxyl)alkyl), and ethers (e.g., alkoxy, aryloxy, alkoxyalkyl, aryloxyalkyl); optionally substituted carbonyl-containing groups, e.g., aldehydes (e.g., carboxaldehyde), ketones (e.g., alkylcarbonyl, alkylcarbonylalkyl, arylcarbonyl, arylalkylcarbonyl, arycarbonylalkyl), carboxy acids (e.g., carboxy, carboxyalkyl), esters (e.g., alkoxycarbonyl, alkoxycarbonylalkyl, alkylcarbonyloxy, alkylcarbonyloxyalkyl), carbonates, thioesters, amides (e.g., aminocarbonyl, mono- or dialkylaminocarbonyl, aminocarbonylalkyl, mono- or dialkylaminocarbonylalkyl, arylaminocarbonyl, alkylarylaminocarbonyl), carbamates (e.g., alkoxycarbonylamino, arloxycarbonylamino, aminocarbonyloxy, mono- or dialkylaminocarbonyloxy, arylaminocarbonyloxy, alkylarylaminocarbonyloxy), and ureas (e.g., mono- or dialkylaminocarbonylamino, arylaminocarbonylamino, alkylarylaminocarbonylamino); optionally substituted groups containing carbonyl derivatives, e.g., imines, oximes, and thioureas; optionally substituted nitrogen-containing groups, e.g., amines (e.g., amino, mono- or dialkylamino, mono- or diarylamino, alkylarylamino, aminoalkyl, mono- or dialkylaminoalkyl), azides, nitriles (e.g., cyano, cyanoalkyl) and nitro; optionally substituted sulfur-containing groups, e.g., thiols, sulfides, thioethers, sulfoxides, sulfones and sulfonamides (e.g. sulfhydryl, alkylthio, alkylsulfinyl, alkylsulfonyl, alkylthioalkyl, alkylsulfinylalkyl, alkylsulfonylalkyl, arylthio, arylsulfinyl, arylsulfonyl, arylthioalkyl, arylsulfinylalkyl, arylsulfonylalkyl); and optionally substituted aromatic or non-aromatic heterocyclic groups containing one or more heteroatoms selected from O, S and N (e.g., thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthyridinyl, cinnolinyl, quinazolinyl, pyridopyridyl, benzoxazinyl, quinoxalinyl, chromenyl, chromanyl, isochromanyl, phthalazinyl, carbolinyl).

Embodiments of the Invention

Composition and Polymer

The embodiments of the present invention are designed to possess certain advantages over conventional biodegradable polymers used to make implantable devices. The degradation rate of a polymer may be enhanced by the appropriate selection of monomers and ratio thereof for the "hard" and "soft" blocks of the polymer. The relatively high $T_g$ or $T_m$ of the "hard" blocks, above body temperature, increases the strength and rigidity of the polymer. Further, the fracture toughness, flexibility and drug permeability of the polymer may be increased by incorporation, with the hard block polymers, of a "soft" block polymer having a $T_g$ less than the $T_g$ or $T_m$ of the hard block polymers. The hard and/or soft blocks may comprise another polymer that may be miscible or immiscible with the soft and/or hard block polymers, respectively. Finally, adhesion of a polymeric coating to a metal surface can be promoted by appropriate (e.g., chemical) modification of the polymer. Such modification could lead to a single polymer, which could be used as a drug reservoir, with no primer.

Accordingly, one embodiment of the present invention, optionally in combination with one or more other embodiments described herein, is directed to a composition comprising a biodegradable triblock copolymer of the structure A-B-A', wherein:
  the A and A' blocks each independently are hard blocks having a $T_g$ or $T_m$ above body temperature;
  the B block is a soft block having a $T_g$ less than the $T_g$ or $T_m$ of the A and A' blocks;
  the A, B and A' blocks each independently have a polymer number-average molecular weight ($M_n$) from about 1 kDa to about 500 kDa; and
  the A and A' blocks may be the same or different.

In one embodiment, the A and A' blocks each independently have a $T_g$ or $T_m$ above body temperature when the A and A' blocks are hydrated, and the B block has a $T_g$ less than the $T_g$ or $T_m$ of the A and A' blocks when the B block is hydrated. In another embodiment, the A and A' blocks each independently have a $T_g$ or $T_m$ above body temperature when the A and A' blocks are not hydrated, and the B block has a $T_g$ less than the $T_g$ or $T_m$ of the A and A' blocks when the B block is not hydrated.

The A and A' blocks in the triblock copolymer may be the same or different from one another. In an embodiment, optionally in combination with one or more other embodiments described herein, the A and A' blocks are the same. In another embodiment, optionally in combination with one or more other embodiments described herein, the A and A' blocks are different.

The B block may or may not be miscible with the A and A' blocks. In one embodiment, optionally in combination with one or more other embodiments described herein, the B block is partially or completely miscible with the A and A' blocks. In another embodiment, optionally in combination with one or more other embodiments described herein, the B block is partially or completely immiscible with the A and A' blocks.

To provide strength and rigidity, the hard A and A' blocks are formulated so that their $T_g$ or $T_m$ is above body temperature. The $T_g$ or $T_m$ of the A and A' blocks can be tuned to a desired value by appropriate selection of component monomers and adjustment of their ratios and numbers. In certain embodiments, optionally in combination with one or more other embodiments described herein, the $T_g$ or $T_m$ of the A and A' blocks independently ranges from about 35° C. to about 300° C., or from about 40° C. to about 250° C., or from about 50° C. to about 200° C., or from about 60° C. to about 150° C., or from about 70° C. to about 100° C.

High rigidity and strength may be important for implantable devices fabricated with a polymeric material, e.g., for a stent so that the stent can support the walls of a vessel. In addition, the degradation rate of the triblock copolymers may be increased by formulating the A and A' blocks as polymers containing appropriate monomer(s), e.g., poly (glycolide) (PGA) or a glycolide-containing copolymer, as further described below.

Some conventional polymers may have a lower toughness and flexibility than desired, e.g., for use in stent applications. For example, certain glassy, semicrystalline polymers can have a $T_g$ above human body temperature and tend to be brittle under physiological conditions, exhibiting low elongation. "Glassy" refers to a polymer that exhibits a brittle fracture mechanism, in which there is little or no plastic deformation prior to failure. As a result, a stent coating fabricated from such polymers can have insufficient toughness and flexibility for the range of aggressive applications of a coated stent, such as overlapped stents, stent through stent delivery, and bifurcations.

Some conventional polymers may also be unable to control drug release. For a polymer with low permeability of a drug, a high drug/polymer ratio must be employed to get the drug to release. However, a high drug/polymer ratio can lead to a drug-release profile in which most of the drug is released as a burst, and the remaining portion of the drug is released very slowly. On the other hand, a low drug/polymer ratio may result in no drug release at all.

To increase fracture toughness and flexibility and to improve drug-release control, the B block of the inventive triblock copolymer is formulated to have a $T_g$ less than the $T_g$ or $T_m$ of the hard A and A' blocks. The $T_g$ of the B block can be tuned to a desired value by appropriate selection of component monomers and adjustment of their ratios and numbers. In some embodiments, the B block has a $T_g$ below body temperature. In further embodiments, optionally in combination with one or more other embodiments described herein, the $T_g$ of the B block ranges from about −70° C. to about 150° C., or from about −50° C. to about 100° C., or from about −25° C. to about 75° C., or from about 0° C. to about 50° C. It should be understood that in some cases, the B block may have a $T_m$ rather than a $T_g$, and the scope of the present invention encompasses cases where the B block has a $T_m$ rather than a $T_g$.

The soft block may have greater flexibility, a lower modulus, and higher fracture toughness than the hard blocks at physiological conditions. It is believed that when a device is placed under stress, the soft block tends to absorb energy when a fracture starts to propagate through the device. Crack propagation through the hard blocks may then be reduced or inhibited. As a consequence, the fracture toughness of the polymeric material, and thus that of the device fabricated therewith, tend to be increased.

In one embodiment, optionally in combination with one or more other embodiments described herein, the tensile modulus of the hard A and A' blocks independently is greater than about 1,000 MPa, and the tensile modulus of the soft B block is less than about 1,000 MPa. In a narrower embodiment, the tensile modulus of the hard A and A' blocks independently is greater than about 1,500 MPa, and the tensile modulus of the soft B block is less than about 750 MPa. In a still narrower embodiment, the tensile modulus of the hard A and A' blocks independently is greater than about 2,000 MPa, and the tensile modulus of the soft B block is less than about 500 MPa.

The soft B block of the triblock copolymer may be composed of a rubbery or elastomeric polymer. An "elastomeric" or "rubbery" polymer refers to a polymer that exhibits elastic deformation through all or most of a range of deformation. The soft B block may also be substantially or completely amorphous. For example, the B block can have a degree of crystallinity of about 10% or less.

Examples of biodegradable polymers having a relatively high fracture toughness at body temperature include, but are not limited to, polycaprolactone (PCL), poly(trimethylene carbonate) (PTMC), polydioxanone, poly(propiolactone), poly(valerolactone) and polyacetal. Accordingly, some embodiments of the soft B block of the triblock copolymer can include caprolactone (CL), trimethylene carbonate (TMC), dioxanone, propiolactone, valerolactone or acetal monomer units, or a combination thereof.

Within the polymer chain, the hard blocks are anchored to the soft block through covalent bonds. In systems where the A, A' and B blocks have some degree of immiscibility, different domains, rich in soft blocks or hard blocks, form within the bulk polymer. These domains are bound to each other via the polymer chains they share. Hence, there is good adhesion between the hard and soft blocks. The high degree of adhesion provided by the covalent bonding facilitates energy transfer between the hard and soft blocks, and thus increases the fracture toughness of the triblock copolymer. It is believed that without the anchoring or adhesion provided by the covalent bonding, a propagating crack may go around the soft block, reducing the effectiveness of the soft block in absorbing energy imparted to a device.

When the hard and soft blocks phase-separate, various morphologies may be formed. The specific morphology formed depends on the relative amounts of the hard and soft blocks, as well as their chemical nature. In general, when the soft block comprises a small volume fraction of the polymer, it tends to exist as a dispersed phase in a continuous phase of the hard block(s). When the hard block comprises a small volume fraction, it tends to exist as a dispersed phase in a continuous phase of soft block. Variations of the ratio of soft to hard blocks allow one to tune/modify the properties of the polymeric material, e.g., the drug permeability and drug-release rate of the material.

The degradation rate of the triblock copolymers can be influenced by the physical state of the hard and soft blocks. Since the diffusion rate of fluids through an amorphous structure is generally faster than through a crystalline structure, the hard blocks and/or soft block may exhibit a higher degree of amorphousness to increase the degradation rate. The faster degrading hard blocks and/or soft block increase water penetration and content in those blocks. The increased water penetration and content causes an increase in the degradation rate of the polymeric material and thus the device.

The degradation rate of the triblock copolymers can also be influenced by the identity of the monomer units making up the hard and soft blocks. For example, the hard blocks and/or soft block may include units that are hydrophilic and/or hydrolytically active. These two characteristics increase the moisture content of the polymeric material, which increases the degradation rate of the polymer. Additionally, the hard blocks and/or soft block may also contain units that have acidic or hydrophilic degradation products. Since the rate of the hydrolysis reaction tends to increase as the pH decreases, acidic degradation products can increase the degradation rate of the polymeric material and hence the device.

As an illustrative example, faster degrading polymers may contain the glycolide (GA) monomer. When incorporated into a polymer, glycolic acid hydrolyzes faster than L-lactic acid or D-lactic acid, for the ester bond formed from glycolic acid is less sterically hindered than that formed from lactic acid. Further, glycolide units have acidic degradation products that can increase the degradation rate of a glycolide-containing polymeric material. Moreover, glycolic acid is a low molecular weight monomer, so that an appreciable level of glycolic acid means that there is a substantial number of ester bonds formed from glycolic acid in a glycolide-containing polymer, any or all of which can hydrolyze. For example, a fast degrading polymer is poly(glycolide-co-trimethylene carbonate) (P(GA-co-TMC)).

In some embodiments, the soft B block can include toughness-enhancing units and fast degrading units. In more specific embodiments, the soft block may include GA, CL, TMC, valerolactone, propiolactone or acetal units, or a combination thereof. The B block can have alternating or random GA, CL, TMC, valerolactone, propiolactone and acetal units. For example, the B block can be poly(GA-co-CL), poly(GA-co-TMC), or poly(GA-co-TMC-co-CL).

The flexibility, toughness and degradation rate of the soft B block can also be adjusted by the ratio of fast degrading and toughness-enhancing units. For example, as the ratio of CL increases in poly(GA-co-CL), the block copolymer becomes more flexible and tougher.

Further, the degradation rate of the B block, and hence that of the polymeric material, can be increased by increasing the fraction of GA in the B block. In exemplary embodiments, the poly(GA-co-CL) or poly(GA-co-TMC) segments can have greater than 1 wt %, 5 wt %, 20 wt %, 50 wt %, 70 wt % or 80 wt % GA units.

The mechanical properties (e.g., rigidity, strength, toughness and flexibility), degradation rate and drug permeability of the inventive triblock copolymer can be tuned by appropriate selection of the monomer units of the hard and soft blocks, the ratio of the monomers within the blocks, the length or molecular weight of the blocks, the weight ratio of the blocks, and any other substances chemically or non-chemically incorporated with the triblock copolymer.

For forming films, the entire polymer needs to have sufficient molecular weight. Accordingly, in some embodiments, optionally in combination with one or more other embodiments described herein, the triblock copolymers have a polymer number-average molecular weight ($M_n$) of at least about 20 kDa. In other embodiments, the triblock copolymers have an $M_n$ of at least about 40 kDa.

In an embodiment, optionally in combination with one or more other embodiments described herein, the triblock copolymers range in $M_n$ from about 20 kDa to about 1,000 kDa. In another embodiment, the triblock copolymers range in $M_n$ from about 20 kDa to about 500 kDa. A polymer with an $M_n$ from about 20 kDa to about 500 kDa may be more amenable to being processed into a coating. In yet another embodiment, the triblock copolymers range in $M_n$ from about 40 kDa to about 500 kDa.

For the blocks to form discrete phases which are indicative of an immiscible system, they need to be of a certain minimal size. When a two-phase system forms, each phase is saturated with the other phase, although these saturated concentrations may be very small. Accordingly, in some embodiments, the A, A' and B blocks each independently have an $M_n$ of at least about 1 kDa. In certain embodiments, optionally in combination with one or more other embodiments described herein, the A, A' and B blocks each independently range in $M_n$ from about 1 kDa to about 500 kDa, or from about 10 kDa to about 400 kDa, or from about 20 kDa to about 300 kDa, or from about 30 kDa to about 200 kDa, or from about 40 kDa to about 100 kDa.

In further embodiments, optionally in combination with one or more other embodiments described herein, the ratio of the molecular weight of each of the A and A' blocks to the B block is between about 20:1 and about 1:20, more narrowly between about 10:1 and about 1:10, and still more narrowly between about 5:1 and about 1:5.

In other embodiments, optionally in combination with one or more other embodiments described herein, the weight fraction of the A and A' blocks with respect to the total triblock copolymer is from about 1% to about 99%, more narrowly from about 10% to about 90%, still more narrowly from about 20% to about 80%, even more narrowly from about 30% to about 70%, and still even more narrowly from about 40% to about 60%. In yet other embodiments, the triblock copolymer can contain about 1-30 wt %, or more narrowly about 2-20 wt %, of the B block and about 70-99% wt %, or 80-98 wt %, of the A and A' blocks.

In yet other embodiments, optionally in combination with one or more other embodiments described herein, the A, B and A' blocks each independently comprise a polymer comprising from one to four different types of monomer, wherein each type of monomer has from about 5 to about 5,000 monomer units. In narrower embodiments, each type of monomer in the polymer of the A, B or A' block independently has from about 10 to about 4,500 monomer units, or from about 20 to about 4,000 monomer units, or from about 30 to about 3,500 monomer units, or from about 40 to about 3,000 monomer units, or from about 50 to about 2,500 monomer units.

According to further embodiments of the present invention, optionally in combination with one or more other embodiments described herein:
the A and A' blocks each independently comprise a polymer selected from the group consisting of poly(L-lactide) (PLLA), poly(D,L-lactide), poly(glycolide) (PGA), poly(GA-co-D,L-lactide), poly(GA-co-L-lactide), and any variations in the arrangement of the monomers thereof; and
the B block comprises a polymer selected from the group consisting of poly(caprolactone) (PCL), poly(CL-co-GA), poly(trimethylene carbonate) (PTMC), poly(TMC-co-GA), poly(TMC-co-D,L-lactide), poly(TMC-co-L-lactide), poly(TMC-co-CL), poly(TMC-co-D,L-lactide-co-GA), poly(TMC-co-CL-co-GA), poly(dioxanone), poly(TMC-co-dioxanone), poly(dioxanone-co-CL), poly(dioxanone-co-D,L-lactide), poly(dioxanone-co-L-lactide), poly(dioxanone-co-GA), poly(dioxanone-co-D,L-lactide-co-GA), polyketals, and any variations in the arrangement of the monomers thereof.

In some embodiments, optionally in combination with one or more other embodiments described herein, the A, A' and B blocks specifically cannot comprise one or more of any of the aforementioned polymers.

The A and A' blocks can comprise PGA or a glycolide-containing copolymer to achieve fast degradation. To provide strength and rigidity, the hard A and A' blocks are formulated so that their $T_g$ or $T_m$ is above body temperature. In some embodiments, if the A and/or the A' blocks comprise poly(L-lactide) or poly(D,L-lactide), then the B block comprises a glycolide-containing polymer.

To increase fracture toughness, flexibility and drug permeability, the B block is formulated to have a $T_g$ less than the $T_g$ or $T_m$ of the A and A' blocks. In some embodiments, the B block has a $T_g$ below body temperature. For example, poly(TMC) has a $T_g$ of $-15°$ C., and poly(dioxanone) has a $T_g$ of $-10°$ C. to $0°$ C. The B block may be formulated to be miscible or immiscible with the A and A' blocks. In some embodiments, the B block is immiscible with the A and A' blocks.

In an embodiment, optionally in combination with one or more other embodiments described herein, the polyketal polymer of the B block has the structure of

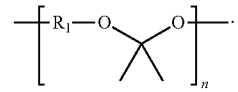

According to one embodiment, optionally in combination with one or more other embodiments described herein, $R_1$ is a poly(caprolactone) diol or a $C_2$-$C_{24}$ diol of the structure, —O—$R_2$—, that contains an optionally substituted aliphatic, heteroaliphatic, cycloaliphatic, heterocycloaliphatic, aromatic or heteroaromatic group, or a combination thereof, and n is an integer from about 5 to about 5,000.

In narrower embodiments, n for the polyketal polymer is an integer from about 10 to about 4,500, or from about 20 to about 4,000, or from about 30 to about 3,500, or from about 40 to about 3,000, or from about 50 to about 2,500.

In an embodiment, optionally in combination with one or more other embodiments described herein, the polyketal polymer has a polymer number-average molecular weight ($M_n$) from about 0.5 kDa to about 500 kDa. In narrower embodiments, the polyketal polymer has an $M_n$ in the range from about 1 kDa to about 500 kDa, or from about 10 kDa to about 400 kDa, or from about 20 kDa to about 300 kDa, or from about 30 kDa to about 200 kDa, or from about 40 kDa to about 100 kDa.

In a further embodiment, $R_1$ is a poly(caprolactone) diol. In other embodiments, $R_1$ is a $C_2$-$C_{24}$ diol, more narrowly a $C_2$-$C_{16}$ diol, or even more narrowly a $C_2$-$C_8$ diol.

One of ordinary skill in the art would understand the structural nature of $R_1$ in light of the definition of "aliphatic", "heteroaliphatic", "cycloaliphatic", "heterocycloaliphatic", "aromatic" and "heteroaromatic" provided earlier. In some embodiments, optionally in combination with one or more other embodiments described herein, the $R_1$ diol specifically cannot be any particular one of the various diols that fall within the genus of the $R_1$ diol, as defined herein. In a particular embodiment, the $R_1$ diol specifically cannot be a poly(caprolactone) diol.

The polyketal polymer of the B block possesses properties that make it a suitable component of the inventive biodegradable triblock copolymer. The ketal linkages in the backbone of the polyketal polymer undergo rapid acid-catalyzed hydrolysis. The degradation products, $C_2$-$C_{24}$ HO—$R_1$—OH and acetone, are low molecular weight, excretable compounds that in many cases are water-soluble and not acidic. Thus, the polyketal polymer is an acid-sensitive, biodegradable polymer that is expected to release an incorporated drug at an accelerated rate in acidic environments. The polyketal polymer may degrade faster than some polymers (e.g., PLGA), but more slowly than other polymers (e.g., poly(ortho esters) and poly(β-amino esters)), thereby permitting the tuning of drug-release rates to a particular application.

Selection of a different $R_1$ group gives a polyketal polymer having a different $T_g$, and thus allows for the tuning of the flexibility and toughness of the polymer. Further, selection of different $R_1$ groups differing in their degree of lipophilicity and steric bulkiness yields polyketal polymers differing in hydrophobicity/hydrophilicity and steric hindrance around the ketal linkages. This would affect the degradation rate and the drug-release rate of the triblock copolymer containing the polyketal polymer.

Poly(caprolactone) can be a flexible polymer having a $T_g$ of about −60° C. (the $T_g/T_m$ of PCL is tunable depending on, e.g., its molecular weight). PCL may also be tuned to degrade more slowly, e.g., in about 1-2 years. Therefore, the use of poly(caprolactone) diol as the $R_1$ diol can result in a polyketal that is softer and more flexible, but degrades more slowly, than polyketals based on an aromatic $R_1$ diol (e.g., 1,4-benzenedimethanol).

The polyketal polymer may be synthesized by any of various methods known in the art. For example, the polyketal polymer may be synthesized by acid-catalyzed polycondensation of the diol, HO—$R_1$—OH, with an acetone source such as acetone or 2,2-dimethoxypropane. The synthesis may be done in the presence of excess diol, which would result in a hydroxyl-terminated polymer segment that may be used to initiate growth of other segments of the B block or growth of the A and A' blocks by ring-opening polymerization.

Advantages of the A-B-A' triblock copolymers of the present invention (e.g., poly(GA-ran-LLA)-block-poly(TMC)-block-poly(GA-ran-LLA)) over conventional biodegradable polymers include, but are not limited to:

The degradation rates of the inventive triblock copolymers (e.g., glycolide-containing polymers) can be tunable such that the polymers completely or substantially completely degrade over a desired period of time (e.g., one year or less).

The triblock structure can permit a degree of tuning of the mechanical properties (e.g., strength, rigidity, toughness, flexibility and elongation) of the triblock polymers by selection of the appropriate monomer components of the A, B and A' blocks and by variation of the molecular weights of the blocks and the relative ratios of the monomers within the blocks.

Because the soft B block has a $T_g$ less than the $T_g$ or $T_m$ of the A and A' blocks, it can provide a higher permeability to drugs than the A and A' blocks. Therefore, the triblock copolymers of the invention can have a higher drug permeability than polymers formed of the A and A' blocks only, e.g., pure poly(D,L-lactide-co-glycolide) (PLGA). The higher drug permeability can allow better control of drug-release rates at reasonable drug-to-polymer ratios, e.g., where the amount of polymer is greater than 50% by weight.

An additional advantage of the inventive triblock copolymers is their compatibility with terminal sterilization techniques. Various terminal sterilization processes are available for sterilizing implantable devices such as drug-delivery stents. Many of these processes, such as electron beam and gamma irradiation, can cause degradation of the drug. Ethylene oxide gas (EOG) tends to cause less drug degradation. During EOG sterilization, however, the drug-delivery coating is exposed to a combination of heat, humidity and EOG. With many conventional biodegradable polymers, such a combination of conditions softens the coating, leading to coating flow and deformation. Unlike some biodegradable polymeric coatings, the triblock copolymers of the invention are compatible with EOG sterilization.

Some polymers also cannot adhere to metal surfaces. For a polymer that does not have any inherent adhesion to metal surfaces, a primer of that pure polymer may have to be used to achieve optimum adhesion to metal stents.

The triblock copolymers of the invention have characteristics that improve their adhesion to metal surfaces. For example, the B block with a lower $T_g$ is expected to interact favorably with a metal substrate at body temperature. Moreover, the different polarity of the hard A and A' blocks and the soft B block increases the chance of favorable non-covalent adhesive interactions with metal substrates.

To improve adhesion of the triblock copolymers to metal surfaces, at least one dihydroxyaryl group could be conjugated to the polymer ends of the triblock copolymers. The dihydroxyaryl group(s) may contain a dihydroxyphenyl moiety. Ortho-dihydroxyphenyl groups in 3,4-dihydroxyphenyl alanine have been shown to be responsible for the bonding of mussel adhesive proteins to a variety of metallic substrates. B. P. Lee et al., *Biomacromolecules*, 3: 1038-1047 (2002). Other 3,4-dihydroxyphenyl-containing compounds that may be conjugated to the polymer ends of the triblock copolymers to increase their adhesion to metal surfaces include, e.g., dopamine and 3,4-dihydroxyhydrocinnamic acid.

Accordingly, in some embodiments, optionally in combination with one or more other embodiments described herein, at least one dihydroxyaryl group is conjugated to the polymer ends of the triblock copolymer. In an embodiment, the at least one dihydroxyaryl group contains an ortho-dihydroxyphenyl moiety. In one embodiment, the at least one dihydroxyaryl group contains a 1,2-dihydroxyphenyl moiety. In another embodiment, the at least one dihydroxyaryl group contains a 3,4-dihydroxyphenyl moiety. 3,4-Dihydroxyphenyl-containing compounds that could be conjugated to the polymer ends of a triblock copolymer include, e.g., dopamine and 3,4-dihydroxyhydrocinnamic acid.

Biocompatible Moieties

Another embodiment of the invention, optionally in combination with one or more other embodiments described herein, is drawn to a composition comprising an A-B-A' triblock copolymer of the invention and at least one biologically compatible (or "biocompatible") moiety. The at least one biocompatible moiety may be blended or bonded with the triblock copolymer. If bonded with the triblock copolymer, the biocompatible moiety may be included in the A, B and/or A' bocks, providing the ABA' triblock copolymer with biological, e.g., blood, compatibility. The biocompatible moieties may be selected in such a way as to make the entire ABA' triblock copolymer biologically degradable.

Examples of suitable biocompatible moieties include, but are not limited to, poly(alkylene glycols), e.g., poly(ethylene glycol) (PEG), poly(ethylene oxide), poly(propylene glycol) (PPG), poly(tetramethylene glycol) and poly(ethylene oxide-co-propylene oxide); lactones and lactides, e.g., ε-caprolactone, β-butyrolactone, δ-valerolactone and glycolide; poly(N-vinyl pyrrolidone); poly(acrylamide methyl propane sulfonic acid) and salts thereof (AMPS and salts thereof); poly(styrene sulfonate); sulfonated dextran; polyphosphazenes; poly(orthoesters); poly(tyrosine carbonate); sialic acid; hyaluronic acid; hyaluronic acid having a stearoyl or palmitoyl substituent group; copolymers of PEG with hyaluronic acid, hyaluronic acid-stearoyl or hyaluronic acid-palmitoyl; heparin; copolymers of PEG with heparin; a graft copolymer of poly(L-lysine) and PEG; or copolymers thereof. The molecular weight of a biocompatible polymeric moiety may be below 40 kDa to ensure renal clearance of the compound, e.g., between about 300 and about 40,000 Daltons, or between about 8,000 and about 30,000 Daltons, e.g., about 15,000 Daltons.

Accordingly, in one embodiment, the at least one biocompatible moiety is selected from the group consisting of poly(ethylene oxide), poly(propylene glycol), poly(tetramethylene glycol), polyethylene oxide-co-propylene oxide), ε-caprolactone, β-butyrolactone, δ-valerolactone, glycolide, poly(N-vinyl pyrrolidone), poly(acrylamide methyl propane sulfonic acid) and salts thereof, poly(styrene sulfonate), sulfonated dextran, polyphosphazenes, poly(orthoesters), poly(tyrosine carbonate), sialic acid, hyaluronic acid or derivatives thereof, copolymers of poly(ethylene glycol) with hyaluronic acid or derivatives thereof, heparin, copolymers of polyethylene glycol with heparin, a graft copolymer of poly(L-lysine) and poly(ethylene glycol), and copolymers thereof.

In some embodiments, optionally in combination with one or more other embodiments described herein, the at least one biocompatible moiety specifically cannot be one or more of any of the biocompatible moieties described herein.

Biologically Absorbable Polymers

Yet another embodiment of the invention, optionally in combination with one or more other embodiments described herein, is directed to a composition comprising an A-B-A' triblock copolymer of the invention and at least one additional biologically absorbable polymer. The at least one additional bioabsorbable polymer may impart desired properties to the composition. Such a polymer may be blended or bonded with the triblock copolymer.

Examples of biologically absorbable polymers include, but are not limited to:
(1) poly(hydroxybutyrate) (PHB);
(2) poly(hydroxyvalerate) (PHV);
(3) poly(hydroxybutyrate-co-valerate) (PHB-HV);
(4) poly(caprolactone) (PCL);
(5) poly(lactide-co-glycolide) (PLGA);
(6) ABA triblock copolymers of PEG with poly(butylene terephthalate) (PBT), e.g., poly(ethylene-glycol)-block-poly(butyleneterephthalate) (PEG-PBT), poly (ethylene-glycol)-block-poly (butylene terephthalate)-block-poly(ethylene-glycol) (PEG-PBT-PEG), and poly(butyleneterephthalate)-block-poly(ethylene-glycol)-block poly(butyleneterephthalate) (PBT-PEG-PBT); and
(7) ABA triblock copolymers of PEG with PCL, e.g., poly(ethylene-glycol)-block-poly(caprolactone) (PEG-PCL), poly(ethylene-glycol)-block-poly(caprolactone)-block-poly(ethylene-glycol) (PEG-PCL-PEG), and poly(caprolactone)-block-poly(ethylene-glycol)-block-poly(caprolactone) (PCL-PEG-PCL).

Any combination of bioabsorbable polymers of groups (1)-(7) above may also be used. PEG-PBT and PEG-PBT-PEG block copolymers are known under the trade name POLYACTIVE™ and are available from IsoTis Corp. of Holland. These polymers can be obtained, e.g., by transesterification of dibutyleneterephthalate with PEG. In POLYACTIVE™, the ratio between the units derived from ethylene glycol and the units derived from butylene terephthalate can be between about 0.67:1 and about 9:1. The molecular weight of the units derived from ethylene glycol can be between about 300 and about 4,000 Daltons, and the molecular weight of the units derived from butylene terephthalate can be between about 50,000 and about 250,000, e.g., about 100,000 Daltons.

DLPLA-PEG-DLPLA, PEG-DLPLA-PEG, PEG-PBT, PEG-PBT-PEG, PBT-PEG-PBT, PEG-PCL, PEG-PCL-PEG, and PCL-PEG-PCL block copolymers all contain fragments with ester bonds. Ester bonds are known to be water-labile bonds. When in contact with slightly alkaline blood, ester bonds are subject to base-catalyzed hydrolysis, thus ensuring biological degradability of the block copolymers. One product of degradation of every block polymer belonging to the group of DLPLA-PEG-DLPLA, PEG-DLPLA-PEG, PEG-PBT, PEG-PBT-PEG, PBT-PEG-PBT, PEG-PCL, PEG-PCL-PEG, and PCL-PEG-PCL is expected to be PEG, which is highly biologically compatible.

Accordingly, in an embodiment, the at least one additional biologically absorbable polymer is selected from the group consisting of poly(hydroxybutyrate), poly(hydroxyvalerate), poly(hydroxybutyrate-co-valerate), poly(caprolactone), poly(lactide-co-glycolide), poly(ethylene-glycol)-block-poly(butyleneterephthalate), poly(ethylene-glycol)-block-poly(butylene terephthalate)-block-polyethylene-glycol), poly(butyleneterephthalate)-block-poly(ethylene-glycol)-block poly(butyleneterephthalate), poly(ethylene-glycol)-block-poly(caprolactone), poly(ethylene-glycol)-block-poly (caprolactone)-block-poly(ethylene-glycol), poly (caprolactone)-block-poly(ethylene-glycol)-block-poly (caprolactone), and blends thereof.

In some embodiments, optionally in combination with one or more other embodiments described herein, the at least one additional biologically absorbable polymer specifically cannot be one or more of any of the bioabsorbable polymers described herein.

Biologically Active Agents

A further embodiment of the invention, optionally in combination with one or more other embodiments described herein, is directed to a composition comprising an A-B-A' triblock copolymer of the invention and at least one biologically active (or "bioactive") agent. The at least one biologically active agent may include any substance capable of exerting a therapeutic, prophylactic or diagnostic effect for a patient.

Examples of suitable bioactive agents include, but are not limited to, synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules that bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. The bioactive agents could be designed, e.g., to inhibit the activity of vascular smooth muscle cells. They could be directed at inhibiting abnormal or inappropriate migration and/or proliferation of smooth muscle cells to inhibit restenosis.

In an embodiment, the inventive composition comprises at least one biologically active agent selected from the group consisting of antiproliferative, antineoplastic, antimitotic, anti-inflammatory, antiplatelet, anticoagulant, antifibrin, antithrombin, antibiotic, antiallergic and antioxidant substances.

An antiproliferative agent can be a natural proteineous agent such as a cytotoxin or a synthetic molecule. Examples of antiproliferative substances include, but are not limited to, actinomycin D or derivatives and analogs thereof (manufactured by Sigma-Aldrich, or COSMEGEN available from Merck) (synonyms of actinomycin D include dactinomycin, actinomycin IV, actinomycin $I_1$, actinomycin $X_1$, and actinomycin $C_1$); all taxoids such as taxols, docetaxel, and paclitaxel and derivatives thereof; all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Examples of rapamycin derivatives include, but are not limited to, 40-O-(2-hydroxy)ethyl-rapamycin (trade name everolimus from Novartis), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus, manufactured by Abbott Labs.), prodrugs thereof, co-drugs thereof, and combinations thereof.

An anti-inflammatory drug can be a steroidal anti-inflammatory drug, a nonsteroidal anti-inflammatory drug (NSAID), or a combination thereof. Examples of anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol, clobetasol propionate, clobetasone butyrate, clopirac, cloticasone propionate, cormethasone acetate, cortodoxone, deflazacort, desonide, desoximetasone, dexamethasone, dexamethasone acetate, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

Alternatively, the anti-inflammatory agent may be a biological inhibitor of pro-inflammatory signaling molecules. Anti-inflammatory biological agents include antibodies to such biological inflammatory signaling molecules.

In addition, the bioactive agents can be other than antiproliferative or anti-inflammatory agents. The bioactive agents can be any agent that is a therapeutic, prophylactic or diagnostic agent. In some embodiments, such agents may be used in combination with antiproliferative or anti-inflammatory agents. These bioactive agents can also have antiproliferative and/or anti-inflammatory properties or can have other properties such as antineoplastic, antimitotic, cystostatic, antiplatelet, anticoagulant, antifibrin, antithrombin, antibiotic, antiallergic, and/or antioxidant properties.

Examples of antineoplastics and/or antimitotics include, but are not limited to, paclitaxel (e.g., TAXOL® available from Bristol-Myers Squibb), docetaxel (e.g., Taxotere® from Aventis), methotrexate, azathioprine, vincristine, vinblastine, fluorouracil, doxorubicin hydrochloride (e.g., Adriamycin® from Pfizer), and mitomycin (e.g., Mutamycin® from Bristol-Myers Squibb).

Examples of antiplatelet, anticoagulant, antifibrin, and antithrombin agents that may also have cytostatic or antiproliferative properties include, but are not limited to, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as ANGIOMAX (bivalirudin, from Biogen), calcium channel blockers (e.g., nifedipine), colchicine, fibroblast growth factor (FGF) antagonists, fish oil (e.g., omega 3-fatty acid), histamine antagonists, lovastatin (a cholesterol-lowering drug that inhibits HMG-CoA reductase, brand name Mevacor® from Merck), monoclonal antibodies (e.g., those specific for platelet-derived growth factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetics, 4-amino-2,2,6,6-tetramethylpiperidine-1-oxyl (4-amino-TEMPO), estradiol, anticancer agents, dietary supplements such as various vitamins, and a combination thereof.

Examples of cytostatic substances include, but are not limited to, angiopeptin, angiotensin converting enzyme inhibitors such as captopril (e.g., Capoten® and Capozide® from Bristol-Myers Squibb), cilazapril and lisinopril (e.g., Prinivil® and Prinzide® from Merck).

Examples of antiallergic agents include, but are not limited to, permirolast potassium. Examples of antioxidant substances include, but are not limited to, 4-amino-2,2,6,6-tetramethylpiperidine-1-oxyl (4-amino-TEMPO).

Other bioactive agents may include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary vasodilators; peripheral and cerebral vasodilators; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Other biologically active agents that may be used include alpha-interferon, genetically engineered epithelial cells, tacrolimus and dexamethasone.

A "prohealing" drug or agent, in the context of a blood-contacting implantable device, refers to a drug or agent that has the property that it promotes or enhances re-endothelialization of arterial lumen to promote healing of the vascular tissue. The portion(s) of an implantable device (e.g., a stent) containing a prohealing drug or agent can attract, bind and eventually become encapsulated by endothelial cells (e.g., endothelial progenitor cells). The attraction, binding, and encapsulation of the cells will reduce or prevent the formation of emboli or thrombi due to the loss of the mechanical properties that could occur if the stent was insufficiently encapsulated. The enhanced re-endothelialization may promote the endothelialization at a rate faster than the loss of mechanical properties of the stent.

The prohealing drug or agent can be dispersed in the body of the bioabsorbable polymer substrate or scaffolding. The prohealing drug or agent can also be dispersed within a bioabsorbable polymer coating over a surface of an implantable device (e.g., a stent).

"Endothelial progenitor cells" refer to primitive cells made in the bone marrow that can enter the bloodstream and go to areas of blood vessel injury to help repair the damage. Endothelial progenitor cells circulate in adult human peripheral blood and are mobilized from bone marrow by cytokines, growth factors, and ischemic conditions. Vascular injury is repaired by both angiogenesis and vasculogenesis mechanisms. Circulating endothelial progenitor cells contribute to repair of injured blood vessels mainly via a vasculogenesis mechanism.

In some embodiments, the prohealing drug or agent can be an endothelial cell (EDC)-binding agent. In certain embodiments, the EDC-binding agent can be a protein, peptide or antibody, which can be, e.g., one of collagen type 1, a 23 peptide fragment known as single chain Fv fragment (scFv A5), a junction membrane protein vascular endothelial (VE)-cadherin, and combinations thereof. Collagen type 1, when bound to osteopontin, has been shown to promote adhesion of endothelial cells and modulate their viability by the down regulation of apoptotic pathways. S. M. Martin, et al., *J. Biomed. Mater. Res.,* 70A:10-19 (2004). Endothelial cells can be selectively targeted (for the targeted delivery of immunoliposomes) using scFv A5. T. Volkel, et al., *Biochimica et Biophysica Acta,* 1663:158-166 (2004). Junction membrane protein vascular endothelial (VE)-cadherin has been shown to bind to endothelial cells and down regulate apoptosis of the endothelial cells. R. Spagnuolo, et al., *Blood,* 103:3005-3012 (2004).

In some embodiments, the EDC-binding agent can be the active fragment of osteopontin, (Asp-Val-Asp-Val-Pro-Asp-Gly-Asp-Ser-Leu-Ala-Tyr-Gly)(SEQ ID NO: 1). Other EDC-binding agents include, but are not limited to, EPC (epithelial cell) antibodies, RGD peptide sequences, RGD mimetics, and combinations thereof.

In further embodiments, the prohealing drug or agent may be a substance or agent that attracts and binds endothelial progenitor cells. Representative substances or agents that attract and bind endothelial progenitor cells include antibodies such as CD-34, CD-133 and vegf type 2 receptor. An agent that attracts and binds endothelial progenitor cells can include a polymer having nitric oxide donor groups.

The foregoing biologically active agents are listed by way of example and are not meant to be limiting. Other biologically active agents that are currently available or that may be developed in the future are equally applicable.

In a more specific embodiment, optionally in combination with one or more other embodiments described herein, the composition of the invention comprises at least one biologically active agent selected from the group consisting of paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy] ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, prodrugs thereof, co-drugs thereof, and a combination thereof. In a particular embodiment, the bioactive agent is everolimus. In another specific embodiment, the bioactive agent is clobetasol.

In some embodiments, optionally in combination with one or more other embodiments described herein, the at least one biologically active agent specifically cannot be one or more of any of the bioactive drugs or agents described herein.

Material and Coating

The inventive composition comprising a biodegradable ABA' triblock copolymer may be used to make a material of which an implantable device is formed. Such a material may comprise any combination of embodiments of the inventive composition described herein.

Accordingly, an embodiment of the invention, optionally in combination with one or more other embodiments described herein, is drawn to a material containing any combination of embodiments of the composition comprising a biodegradable ABA' triblock copolymer. For example, the composition forming the material may optionally have at least one dihydroxyaryl group conjugated to the polymer ends of the triblock copolymer and optionally contain at least one biocompatible moiety, at least one additional biologically absorbable polymer, and/or at least one biologically active agent.

The material of the invention may be used to make a portion of an implantable device or the whole device itself. Moreover, the material may be used to make a coating that is disposed over at least a portion of an implantable device.

Accordingly, an embodiment of the invention, optionally in combination with one or more other embodiments described herein, is directed to a coating containing any combination of embodiments of the composition comprising a biodegradable ABA' triblock copolymer. For example, the composition forming the coating may optionally have at least one dihydroxyaryl group conjugated to the polymer ends of the triblock copolymer and optionally contain at least one biocompatible moiety, at least one additional biologically absorbable polymer, and/or at least one biologically active agent.

The coating may have a variety of thickness and biodegradation rates. In some embodiments, optionally in combination with one or more other embodiments described herein, the coating has a thickness of ≤about 30 micron, or ≤about 20 micron, or ≤about 10 micron. In further embodiments, optionally in combination with one or more other embodiments described herein, the biodegradation rate of the coating is characterized by loss of about 100% mass within about two years, or loss of about 100% mass within about 12 months, or loss of at least about 70% mass within about six months.

Implantable Device

The inventive material containing any combination of embodiments of the composition comprising a biodegradable ABA' copolymer may be used to form an implantable device. Accordingly, one embodiment of the invention, optionally in combination with one or more other embodiments described herein, is drawn to an implantable device formed of a material containing any combination of embodiments of the composition comprising a biodegradable ABA' copolymer. For example, the implantable device may be formed of a material comprising a composition that optionally has at least one dihydroxyaryl group conjugated to the polymer ends of the triblock copolymer and optionally contains at least one biocompatible moiety, at least one additional biologically absorbable polymer, and/or at least one biologically active agent.

A portion of the implantable device or the whole device itself may be formed of the material containing any combination of embodiments of the composition comprising a biodegradable ABA' copolymer. Further, at least a portion of the implantable device may be coated by a coating containing any combination of embodiments of the composition comprising a biodegradable ABA' copolymer.

Accordingly, an embodiment of the invention, optionally in combination with one or more other embodiments described herein, is directed to an implantable device formed of a coating containing any combination of embodiments of the composition comprising a biodegradable ABA' copolymer. For example, the implantable device may be formed of a coating comprising a composition that optionally has at least one dihydroxyaryl group conjugated to the polymer ends of the triblock copolymer and optionally contains at least one biocompatible moiety, at least one additional biologically absorbable polymer, and/or at least one biologically active agent.

The implantable device may be formed of a coating that may have a variety of thickness and biodegradation rates. In some embodiments, optionally in combination with one or more other embodiments described herein, the implantable device is formed of a coating that has a thickness of ≤about 30 micron, or ≤about 20 micron, or ≤about 10 micron. In further embodiments, optionally in combination with one or more other embodiments described herein, the implantable device is formed of a coating whose biodegradation rate is characterized by loss of about 100% mass within about two years, or loss of about 100% mass within about 12 months, or loss of at least about 70% mass within about six months.

The present invention also encompasses implantable devices formed of bioabsorbable and/or biostable polymers. In some embodiments, optionally in combination with one or more other embodiments described herein, a portion of the device or the whole device itself can be formed of such polymers and any other substances described herein.

Any implantable device can be formed of the inventive material or coating. Examples of implantable devices include, but are not limited to, stents (e.g., coronary stents and peripheral stents), grafts (e.g., aortic grafts, arteriovenous grafts and by-pass grafts), stent-grafts, catheters, leads and electrodes for pacemakers and defibrillators, endocardial leads (e.g., FINELINE and ENDOTAK, available from Abbott Vascular, Santa Clara, Calif.), clips (e.g., anastomotic clips), shunts (e.g., cerebrospinal fluid and axius coronary shunts), closure devices (e.g., arterial and patent foramen ovale closure devices), and valves (e.g., artificial heart valves).

In an embodiment, optionally in combination with one or more other embodiments described herein, the implantable device is selected from the group consisting of stents, grafts, stent-grafts, catheters, leads and electrodes, clips, shunts, closure devices, and valves. In a more specific embodiment, optionally in combination with one or more other embodiments described herein, the implantable device is a stent. The stent may be balloon-expandable or self-expandable. Moreover, the stent may be intended for any vessel in the body, e.g., neurological, carotid, vein graft, coronary, aortic renal, iliac, femoral, popliteal vasculature and urethral passages.

The underlying structure of the implantable device can be of virtually any design. The device can be made of a metallic material or an alloy such as, but not limited to, cobalt-chromium alloys (e.g., ELGILOY), "L-605", stainless steel (316L), "MP35N," "MP20N," ELASTINITE (Nitinol), tantalum, tantalum-based alloys, nickel-titanium alloys, platinum, platinum-based alloys (e.g., platinum-iridium alloy), iridium, gold, magnesium, titanium, titanium-based alloys, zirconium-based alloys, or combinations thereof "L-605" is a trade name for an alloy of cobalt, chromium, tungsten, nickel and iron available as Haynes 25 from Haynes International (Kokomo, Ind.). "L-605" consists of 51% cobalt, 20% chromium, 15% tungsten, 10% nickel and 3% iron. "MP35N" and "MP20N" are trade names for alloys of cobalt, nickel, chromium and molybdenum available from Standard Press Steel Co. (Jenkintown, Pa.). "MP35N" consists of 35% cobalt, 35% nickel, 20% chromium and 10% molybdenum. "MP20N" consists of 50% cobalt, 20% nickel, 20% chromium and 10% molybdenum.

Structure of Coating

According to embodiments of the invention, optionally in combination with one or more other embodiments described herein, a coating for an implantable device (e.g., a stent) can be a multi-layer structure that may include any of the following four layers or combination thereof:

(1) a primer layer;
(2) a drug-polymer layer (also referred to as a "reservoir" or "reservoir layer") or, alternatively, a polymer-free drug layer;
(3) a topcoat layer; and/or
(4) a finishing coat layer.

Each layer of a stent coating can be disposed over the stent by dissolving the polymer or a blend of polymers in a solvent, or a mixture of solvents, and disposing the resulting polymer solution over the stent by spraying or immersing the stent in the solution. After the solution has been disposed over the stent, the coating is dried by allowing the solvent to evaporate. The process of drying can be accelerated if the drying is conducted at an elevated temperature. The complete stent coating can be optionally annealed at a temperature between about 40° C. and about 150° C. for a period of time between about 5 minutes and about 60 minutes, if desired, to improve the thermodynamic stability of the coating.

To incorporate a drug into the reservoir layer, the drug can be combined with the polymer solution that is disposed over the stent as described above. Alternatively, if it is desirable to have the stent coating with a fast drug-release rate, a polymer-free reservoir can be made. To fabricate a polymer-free reservoir, the drug can be dissolved in a suitable solvent or mixture of solvents, and the resulting drug solution can be disposed over the stent by spraying or immersing the stent in the drug-containing solution.

Instead of introducing a drug via a solution, the drug can be introduced as a colloid system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. Optionally, a surfactant may be added to stabilize the suspension. The suspension can be mixed with a polymer solution and the mixture can be disposed over the stent as described above. Alternatively, the drug suspension can be disposed over the stent without being mixed with the polymer solution.

The drug-polymer layer can be applied directly onto at least a part of the stent surface to serve as a reservoir for at least one bioactive agent or drug that is incorporated into the reservoir layer. The optional primer layer can be applied between the stent and the reservoir to improve the adhesion of the drug-polymer layer to the stent. The optional topcoat layer can be applied over at least a portion of the reservoir layer and serves as a rate-limiting membrane that helps to control the rate of release of the drug. In one embodiment, the topcoat layer can be essentially free from any bioactive agents or drugs. If the topcoat layer is used, the optional finishing coat layer can be applied over at least a portion of the topcoat layer for further control of the drug-release rate and for improving the biocompatibility of the coating. Without the topcoat layer, the finishing coat layer can be deposited directly on the reservoir layer.

The process of the release of a drug from a coating having both topcoat and finishing coat layers includes at least three steps. First, the drug is absorbed by the polymer of the topcoat layer on the drug-polymer layer/topcoat layer interface. Next, the drug diffuses through the topcoat layer using the void volume between the macromolecules of the topcoat layer polymer as pathways for migration. Next, the drug arrives at the topcoat layer/finishing layer interface. Finally, the drug diffuses through the finishing coat layer in a similar fashion, arrives at the outer surface of the finishing coat layer, and desorbs from the outer surface. At this point, the drug is released into the surrounding tissue. Consequently, a combination of the topcoat and finishing coat layers, if used, can serve as a rate-limiting barrier. The drug can be released through the degradation, dissolution, and/or erosion of the layer.

In one embodiment, any or all of the layers of the stent coating can be made of a biologically degradable, erodable, absorbable, and/or resorbable polymer. In another embodiment, the outermost layer of the coating can be limited to such a polymer.

To illustrate in more detail, in a stent coating having all four layers described above (i.e., the primer, the reservoir layer, the topcoat layer and the finishing coat layer), the outermost layer is the finishing coat layer, which is made of a polymer that is biologically degradable, erodable, absorbable, and/or resorbable. In this case, the remaining layers (i.e., the primer, the reservoir layer and the topcoat layer) optionally can also be fabricated of a biologically degradable polymer; the polymer may be the same or different in each layer.

If the finishing coat layer is not used, the topcoat layer can be the outermost layer and is made of a biologically degradable polymer. In this case, the remaining layers (i.e., the primer and the reservoir layer) optionally can also be fabricated of a biologically degradable polymer; the polymer may be the same or different in each of the three layers.

If neither the finishing coat layer nor the topcoat layer is used, the stent coating could have only two layers—the primer and the reservoir. In such a case, the reservoir is the outermost layer of the stent coating and is made of a biologically degradable polymer. The primer optionally can also be fabricated of a biologically degradable polymer. The two layers may be made from the same or different materials.

Increased rate of degradation, erosion, absorption and/or resorption of a biologically degradable, erodable, absorbable and/or resorbable polymer is expected to lead to an increased rate of release of a drug due to the gradual disappearance of the polymer that forms the reservoir or the topcoat layer, or both. Through selection of an appropriate biodegradable polymer, a stent coating can be engineered to provide either fast or slow release of a drug, as desired. Those having ordinary skill in the art can determine whether a stent coating having slow or fast drug-release rate is advisable for a particular drug. For example, fast release may be recommended for stent coatings loaded with anti-migratory drugs, which often need to be released within 1 to 2 weeks. For antiproliferative drugs, slow release may be desired (e.g., up to 30-day release time).

Any layer of a stent coating may contain any amount of the at least one additional biologically absorbable polymer described above, or a blend of more than one such polymer. If less than 100% of the layer is made of the bioabsorbable polymer(s), other alternative polymers can comprise the balance. Examples of alternative polymers that can be employed include, but are not limited to, polyacrylates, e.g., poly(butyl methacrylate), poly(ethyl methacrylate), poly (ethyl methacrylate-co-butyl methacrylate), poly(acrylonitrile), poly(ethylene-co-methyl methacrylate), poly(acrylonitrile-co-styrene) and poly(cyanoacrylates); fluorinated polymers and/or copolymers, e.g., poly(vinylidene fluoride) and poly(vinylidene fluoride-co-hexafluoro propylene); poly (N-vinyl pyrrolidone); polydioxanone; polyorthoester; polyanhydride; poly(glycolic acid); poly(glycolic acid-co-trimethylene carbonate); polyphosphoester; polyphosphoester urethane; poly(amino acids); poly(trimethylene carbonate); poly(iminocarbonate); co-poly(ether-esters); polyalkylene oxalates; polyphosphazenes; biomolecules, e.g., fibrin, fibrinogen, cellulose, starch, collagen and hyaluronic acid; polyurethanes; silicones; polyesters; polyolefins; polyisobutylene and ethylene-alphaolefin copolymers; vinyl halide polymers and copolymers, e.g., polyvinyl chloride; polyvinyl ethers, e.g., polyvinyl methyl ether; polyvinylidene chloride; polyvinyl ketones; polyvinyl aromatics, e.g., polystyrene; polyvinyl esters, e.g., polyvinyl acetate; copolymers of vinyl monomers with each other and olefins, e.g., poly(ethylene-co-vinyl alcohol) (EVAL); ABS resins; poly(ethylene-co-vinyl acetate); polyamides, e.g., Nylon 66 and polycaprolactam; alkyd resins; polycarbonates; polyoxymethylenes; polyimides; polyethers, epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

Method of Fabricating Implantable Device

Other embodiments of the invention, optionally in combination with one or more other embodiments described herein, are drawn to a method of fabricating an implantable device. In one embodiment, the method comprises forming the implantable device of a material containing any combination of embodiments of the composition comprising a biodegradable ABA' copolymer. For example, the method comprises forming the implantable device of a material comprising a composition that optionally has at least one dihydroxyaryl group conjugated to the polymer ends of the triblock copolymer and optionally contains at least one biocompatible moiety, at least one additional biologically absorbable polymer, and/or at least one biologically active agent.

Under the method, a portion of the implantable device or the whole device itself may be formed of the material containing any combination of embodiments of the composition comprising a biodegradable ABA' copolymer. Moreover, the method may comprise depositing over at least a portion of the implantable device a coating containing any combination of embodiments of the composition comprising a biodegradable ABA' copolymer.

Accordingly, in an embodiment, the method comprises disposing over at least a portion of an implantable device a coating containing any combination of embodiments of the composition comprising a biodegradable ABA' copolymer. For example, the method comprises disposing over at least a portion of an implantable device a coating comprising a composition that optionally has at least one dihydroxyaryl group conjugated to the polymer ends of the triblock copolymer and optionally contains at least one biocompatible moiety, at least one additional biologically absorbable polymer, and/or at least one biologically active agent.

The method may deposit a coating having a variety of thickness over an implantable device. In certain embodiments, the method deposits over at least a portion of the implantable device a coating that has a thickness of ≤about 30 micron, or ≤about 20 micron, or ≤about 10 micron.

According to an embodiment, the method is used to fabricate an implantable device selected from the group consisting of stents, grafts, stent-grafts, catheters, leads and electrodes, clips, shunts, closure devices, and valves. In a specific embodiment, the method is used to fabricate a stent.

The triblock copolymer of the invention, and any other desired substances and materials, may be formed into a polymer construct, such as a tube or sheet that can be rolled or bonded to form a construct such as a tube. An implantable device may then be fabricated from the construct. For example, a stent can be fabricated from a tube by laser machining a pattern into the tube. In another embodiment, a polymer construct may be formed from the polymeric material of the invention using an injection-molding apparatus.

In general, representative examples of polymers that may be used to fabricate an implantable device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide), poly(D,L-lactide), poly(caprolactone), poly(trimethylene carbonate), polyethylene amide, polyethylene acrylate, poly(glycolic acid-co-trimethylene carbonate), co-poly(ether-esters) (e.g., PEO/PLA), polyphosphazenes, biomolecules (e.g., fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (e.g., polyvinyl chloride), polyvinyl ethers (e.g., polyvinyl methyl ether), polyvinylidene halides (e.g., polyvinylidene chloride), polyacrylonitrile, polyvinyl ketones, polyvinyl aromatics (e.g., polystyrene), polyvinyl esters (e.g., polyvinyl acetate), acrylonitrile-styrene copolymers, ABS resins, polyamides (e.g., Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be well suited for fabricating an implantable device include ethylene vinyl alcohol copolymer (commonly known by the generic name EVOH or by the trade name EVAL), poly(butyl methacrylate), poly(vinylidene fluoride-co-hexafluoropropylene) (e.g., SOLEF 21508, available from Solvay Solexis PVDF of Thorofare, N.J.), polyvinylidene fluoride (otherwise known as KYNAR, available from Atofina Chemicals of Philadelphia, Pa.), poly(tetrafluoroethylene-co-hexafluoropropylene-co-vinylidene fluoride), ethylene-vinyl acetate copolymers, and polyethylene glycol.

Method of Treating or Preventing Disorders

An implantable device formed of a material or coating containing any combination of embodiments of the composition comprising a biodegradable ABA' copolymer can be used to treat, prevent or diagnose conditions or disorders. Examples of such conditions or disorders include, but are not limited to, atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, bile duct obstruction, ureter obstruction and tumor obstruction.

Accordingly, an embodiment of the invention, optionally in combination with one or more other embodiments described herein, is drawn to a method of treating, preventing or diagnosing a condition or disorder in a patient, comprising implanting in the patient an implantable device formed of a material or coating containing any combination of embodiments of the composition comprising a biodegradable ABA' copolymer. For example, the implantable device may be formed of a material or coating comprising a composition that optionally has at least one dihydroxyaryl group conjugated to the polymer ends of the triblock copolymer and optionally contains at least one biocompatible moiety, at least one additional biologically absorbable polymer, and/or at least one biologically active agent.

In one embodiment, the implantable device is formed of a material or coating containing at least one biologically active agent selected from the group consisting of paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, prodrugs thereof, co-drugs thereof, and a combination thereof.

In an embodiment, the implantable device used in the method is selected from the group consisting of stents, grafts, stent-grafts, catheters, leads and electrodes, clips, shunts, closure devices, and valves. In a specific embodiment, the implantable device is a stent.

According to one embodiment, the condition or disorder treated, prevented or diagnosed by the implantable device is selected from the group consisting of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, bile duct obstruction, ureter obstruction and tumor obstruction.

Synthesis of Triblock Copolymers

The triblock copolymers of the invention can be prepared by any method of polymerization known in the art. Methods of polymerization include, but are not limited to, solution-based polymerization and melt-phase polymerization. In solution-based polymerization, all the reactive components involved in the polymerization reaction are dissolved in a solvent.

In some embodiments of solution-based polymerization, monomer units of the blocks, an initiator, a catalyst and at least one solvent are used. The first step generally involves forming a precursor block, e.g., the B block. Monomer units of the precursor block, a suitable initiator and a suitable catalyst are added to a suitable solvent to form a polymerization solution. After formation of the precursor block, monomer units of the second block (e.g., the A block, or the A and A' blocks if these two blocks are the same) and a catalyst (which may be the same or different than the catalyst used in the first reaction) are then added to the solution to form an AB diblock copolymer or an ABA' triblock copolymer (if the A and A' blocks are the same). If the A and A' blocks are different, then a third reaction to form the A' block may proceed in a similar manner as the second reaction to form the A block. The solvent(s) in the reaction(s) for forming the A and A' blocks can be selected so that the precursor block is soluble in the solvent(s) for the second reaction and the AB diblock is soluble in the solvent(s) for the third reaction, which would facilitate copolymerization of the precursor block and AB diblock with the added units of the A block and the A' block, respectively. In an embodiment, the B block is formed first in the synthesis of a triblock copolymer.

Triblock copolymers can be synthesized by standard methods known to those having ordinary skill in the art, e.g., by ring-opening polymerization (ROP) with the corresponding monomers of the blocks. ROP can be catalyzed by an organic or inorganic acid (including a Lewis acid), an organic or inorganic base (including a Lewis base), an organometallic reagent, and/or heat, if necessary.

One method of synthesizing A-B-A' triblock copolymers of the invention is to conduct ring-opening polymerization (ROP) with the corresponding monomer(s) of the A, B and A' blocks. For example, triblock copolymers in which the A and A' blocks are the same may be produced by performing ROP with the corresponding monomer(s) of the B block, and then performing ROP with the corresponding monomer(s) of the A and A' blocks. An initiating compound containing two active end groups is employed to initiate ROP with the first monomer of the B block. In an embodiment, the two active end groups on the initiating compound are independently a hydroxyl, amino or thiol group.

Likewise, A-B-A' triblock copolymers in which the A and A' blocks are different may be synthesized by:
performing ROP with the corresponding monomer(s) of the B block, wherein an initiating compound containing one active end group and one protected end group is used to initiate ROP with the first monomer of the B block;
performing ROP with the corresponding monomer(s) of the A block;
protecting any active group formed at the polymer end of the A block;
deprotecting the protected end group derived from the initiating compound at the polymer end of the B block;
performing ROP with the corresponding monomer(s) of the A' blocks; and then
optionally deprotecting the protected active group at the polymer end of the A block.

In an embodiment, the active end group on the initiating compound is a hydroxyl, amino or thiol group, and the protected end group on the initiating compound is a protected hydroxyl, amino or thiol group.

In some embodiments, the initiating compounds employed in the synthesis of the triblock copolymers have at least one active end group that is a hydroxyl, amino or thiol group. In an embodiment, the initiating compound is a diol, in which one of the hydroxyl end groups may optionally be protected. In another embodiment, the initiating compound is a diamine, in which one of the amino end groups may optionally be protected. In yet another embodiment, the initiating compound is a dithiol, in which one of the thiol end groups may optionally be protected. In further embodiments, the diamino, dithiol or dihydroxy initiating compound is $C_2$-$C_{24}$ and contains an optionally substituted aliphatic, heteroaliphatic, cycloaliphatic, heterocycloaliphatic, aromatic or heteroaromatic group, or a combination thereof. In other embodiments, the initiating compound is a diol selected from diethylene glycol, triethylene glycol, tetraethylene glycol, poly(ethylene glycol), polypropylene glycol), poly(tetramethylene glycol), and poly(caprolactone) diol.

One example of the synthesis of A-B-A' triblock copolymers, in which the A and A' blocks are the same, via ROP is illustrated by the synthesis of poly(D,L-lactide-co-glycolide-bl-trimethylene carbonate-bl-glycolide-co-D,L-lactide) via ROP in Scheme 1 below.

Scheme 1. Synthesis of poly(D,L-lactide-co-glycolide-bl-trimethylene carbonate-bl-glycolide-co-D,L-lactide) via ring-opening polymerization

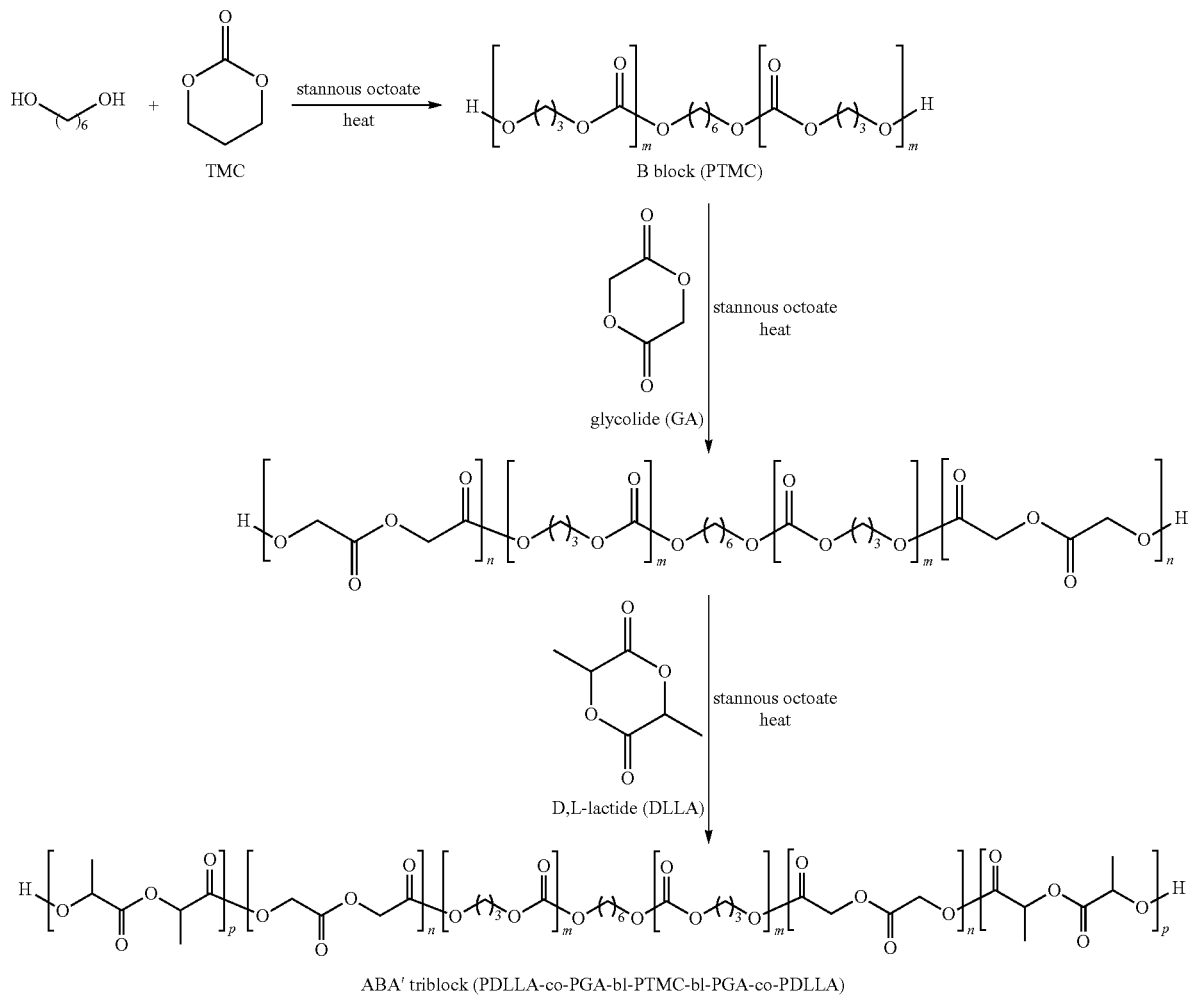

ABA' triblock (PDLLA-co-PGA-bl-PTMC-bl-PGA-co-PDLLA)

In Scheme 1, 1,6-hexanediol is employed to initiate ROP with TMC. The resulting bis(hydroxyl)-terminated B block, PTMC, can then be used to initiate ROP with glycolide, leading to the formation of bis(hydroxyl)-terminated PGA-bl-PTMC-bl-PGA. The A and A' blocks are further elaborated via ROP of this intermediate with a different type of monomer, D,L-lactide, resulting in the triblock copolymer, poly(D,L-lactide-co-glycolide)-block-poly-(trimethylene carbonate)-block-poly(glycolide-co-D,L-lactide). In this example, the A and A' blocks are the same (i.e., poly(glycolide-co-D,L-lactide)), and m, n and p each independently are integers from about 5 to about 5,000. A person of ordinary skill in the art would understand that the synthetic procedure in the above example could also be modified to generate poly(D,L-lactide-ran-glycolide)-block-poly-(trimethylene carbonate)-block-poly(glycolide-ran-D,L-lactide) by conducting ROP in the presence of glycolide and D,L-lactide in the same pot.

The synthesis of triblock copolymers is often done neat, in the absence of a solvent. However, the blocks are not always miscible with each other. For example, in the melt the glycolide may not dissolve in the PTMC polymer. In such a case, polymerization would be conducted in a solvent. If done properly, the intermediate bis(hydroxyl)-terminated PTMC polymer would not need to be isolated and could be used to initiate the next ROP with glycolide.

In the synthesis of a polymer containing a high content of glycolide, a strong or exotic solvent may be needed to initially dissolve the monomer(s). A solvent can usually be employed to dissolve a mixture of monomers into a mixture of monomers and then be evaporated off before an initiating catalyst is added to start the polymerization. The soft B block may also assist in the dissolution of the monomers of the A and A' blocks. In addition, various organo and organometallic catalysts may influence the structure of the polymer by providing different release kinetics and minimize or maximize the polymerization rate of the various monomers incorporated into the A, B or A' block.

The various embodiments of the inventive composition comprising an A-B-A' triblock copolymer, whether the A and A' blocks are the same or different, may be prepared by optionally:

conjugating at least one dihydroxyaryl group to the polymer ends of the triblock copolymer;
blending or bonding at least one biocompatible moiety with the triblock copolymer;
blending or bonding at least one additional biologically absorbable polymer with the triblock copolymer; and
incorporating at least one biologically active agent.

The at least one dihydroxyaryl group may contain, e.g., an ortho-dihydroxyphenyl moiety such as 1,2-dihydroxyphenyl and 3,4-dihydroxyphenyl. 3,4-Dihydroxyphenyl-containing compounds include, e.g., dopamine and 3,4-dihydroxyhydrocinnamic acid. Dopamine could be conjugated to hydroxyl end groups of a triblock copolymer via coupling with 1,1'-carbonyldiimidazole. 3,4-Dihydroxy-hydrocinnamic acid could be conjugated to hydroxyl end groups by conversion of the cinnamic acid to the N-succidimyl ester or by use of dicyclohexylcarbodiimide (DCC) and 4-(dimethylamino)pyridinium (DPTS). Alternatively, conjugation of the cinnamic acid could be effected via a Mitsunobu reaction using triphenylphosphine and diethyl azodicarboxylate (DEAD) or diisopropyl azodicarboxylate (DIAD).

EXAMPLES

The examples set forth below are shown for the sole purpose of further illustrating embodiments of the present invention and are in no way meant to limit the invention. The following prophetic examples are given to aid in understanding the invention, but it is to be understood that the invention is not limited to the particular materials or procedures of the examples.

Example 1

Synthesis of Poly(Glycolide-Ran-D,L-Lactide)-Block-Poly(TMC)-Block-Poly(Glycolide-Ran-D,L-Lactide), 51.8 Mole % Glycolide, 43.6 Mole % Trimethylene Carbonate, and 4.6 Mole % D,L-Lactide A flame-dried, three-neck 250 ml round-bottom flask is charged with 46.41 g (0.455 mole) trimethylene carbonate, 0.123 g (1.16 mmol) distilled diethylene glycol, and 0.053 ml of stannous octoate (0.33 M in toluene) (60,000:1 molar ratio monomer:catalyst). The flask is equipped with a flame-dried mechanical stirrer and adapter for argon purge and vacuum. The reaction vessel is purged by evacuating the flask, followed by venting with argon; this is repeated three times. The reaction flask, under an argon pressure of one atmosphere, is heated to 190° C. and maintained at this temperature for about 16 hours with slow stirring.

In the second stage of polymerization, 6.96 g (48.3 mmol) of D,L-lactide, and 62.64 g (0.54 mole) of molten glycolide, are added to the prepolymer in the reaction flask at 180° C. under a purge of argon. The temperature of the reaction mixture is raised to 230° C. to dissolve the prepolymer into the molten glycolide with gentle stirring. After ten minutes, the temperature is dropped to 200° C. and held there for about two hours with stirring. The polymer is removed from the reactor as a melt and allowed to cool. After grinding, the polymer is dried by heating at 110° C. under a pressure of 0.1 mm Hg for 16 hours to remove any unreacted monomers.

Example 2

Synthesis of Poly(D,L-Lactide)-Block-Poly(Caprolactone-Ran-Glycolide)-Block-Poly(D,L-Lactide), 39.5 Mole % Caprolactone, 34.7 Mole % D,L-Lactide, and 25.8 Mole % Glycolide A flame-dried, three-neck, 250 ml round-bottom flask is charged with 36.0 g (0.316 mole) caprolactone and 24.0 g (0.207 mole) glycolide. The flask is equipped with a flame-dried mechanical stirrer and adapter for argon purge and vacuum. The contents are heated to 120° C. and stirred under vacuum for four hours. After purging with argon, and cooling to room temperature, 0.11 gm (1.4 mmol) distilled diethylene glycol, and 0.097 ml of stannous octoate (0.33 M in toluene) (25,000:1 molar ratio monomer:catalyst), are added. The reaction vessel is purged by evacuating the flask followed by venting with argon; this is repeated three times. The reaction flask, under an argon pressure of one atmosphere, is heated to 180° C. and maintained at this temperature for about 24 hours with slow stirring.

In the second stage of polymerization, 40.0 g (0.278 mole) of D,L-lactide is added to the prepolymer in the reaction flask at 180° C. under a purge of argon. The temperature is raised to 200° C. and held there for about two hours with stirring. The polymer is removed from the reactor as a melt and allowed to cool. After grinding, the polymer is dissolved in chloroform and then precipitated in methanol. Solvent, unreacted monomer, and water are removed by heating the precipitate at 110° C. under a pressure of 0.1 mm Hg for 16 hours.

Example 3

Method of Manufacturing a Drug-Delivery Stent Coating Using the Copolymer of Example 1 or 2

In a first step, an optional primer coating is applied to a stent. A primer solution containing between about 0.1 mass % and about 15 mass %, (e.g., about 2.0 mass %) of the copolymer of Example 1 or 2, and the balance being a solvent mixture of chloroform and 1,1,1-trichloroethane (having about 50 mass % of chloroform and about 50 mass % of 1,1,1-trichloroethane) is prepared. The solution is applied onto the stent to form a primer layer.

To apply the primer layer, a spray apparatus (e.g., Sono-Tek MicroMist spray nozzle, manufactured by Sono-Tek Corp. of Milton, N.Y.) is used. The spray apparatus is an ultrasonic atomizer with a gas entrainment stream. A syringe pump is used to supply the coating solution to the nozzle. The composition is atomized by ultrasonic energy and applied to the stent surfaces. A useful nozzle-to-stent distance is about 20 mm to about 40 mm at an ultrasonic power of about one watt to about two watts. During the process of applying the composition, the stent is optionally rotated about its longitudinal axis, at a speed of about 100 to about 600 rpm, e.g., about 400 rpm. The stent is also linearly moved along the same axis during the application.

The primer solution is applied to a 3.0×12 mm VISION™ stent (available from Abbott Vascular Corp.) in a series of 20-second passes, to deposit, e.g., 20 µg of coating per spray pass. Between the spray passes, the stent is allowed to dry for about 10 seconds to about 30 seconds at ambient temperature. Four spray passes can be applied, followed by baking the primer layer at about 80° C. for about 1 hour. As a result, a primer layer can be formed having a solids content of about 80 µg. For purposes of this example, "solids" means the amount of the dry residue deposited on the stent after all volatile organic compounds (e.g., the solvent) have been removed.

In a manner similar to the application of the primer layer, a polymer-therapeutic solution is prepared and applied using the following formula:
 (a) between about 0.1 mass % and about 15 mass %, (e.g., about 2.0 mass %) of the copolymer of Example 1 or 2;
 (b) between about 0.1 mass % and about 2 mass % (e.g., about 1.0 mass %) of a therapeutic agent. In one embodiment, the therapeutic agent is everolimus (available from Abbott Vascular Corp. of Santa Clara, Calif.); and (c) the balance, a solvent mixture containing about 50 mass % of chloroform and about 50 mass % of 1,1,1-trichloroethane.

The drug-containing formulation is applied to the stent in a manner similar to the application of the copolymer primer layer. The process results in the formation of a drug-polymer reservoir layer having a solids content between about 30 µg and about 750 µg, (e.g., about 175 µg) and a drug content of between about 10 µg and about 250 µg, (e.g., about 55 µg). After application, the coating is baked at 50° C. for two hours to remove any remaining solvent.

While particular embodiments of the present invention have been shown and described, it will be obvious to those skilled in the art that changes and modifications can be made thereto without departing from the invention in its broader aspects. Therefore, the appended claims are to encompass within their scope all such changes and modifications as fall within the true spirit and scope of the present invention.

What is claimed is:

1. An implantable device comprising a coating, the coating comprising a biodegradable triblock copolymer of the structure A-B-A',
wherein:
the A and A' blocks each independently are hard blocks having a $T_g$ or $T_m$ above body temperature;
the B block is a soft block having a $T_g$ less than the $T_g$ or $T_m$ of the A and A' blocks;
the A, B and A' blocks each independently have a polymer number-average molecular weight ($M_n$) from about 1 kDa to about 500 kDa;
the A and A' blocks may be the same or different; and
the B block comprises a polyketal polymer of the structure:

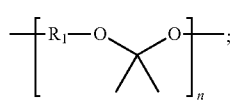

wherein:
$R_1$ is a poly(caprolactone) diol or a $C_2$-$C_{24}$ diol of the structure, —O—$R_2$—, where $R_2$ is an optionally substituted aliphatic, heteroaliphatic, cycloaliphatic, heterocycloaliphatic, aromatic or heteroaromatic group, a residue thereof, or a combination thereof; and
n is an integer from about 5 to about 5,000.

2. The implantable device of claim 1, wherein the tensile modulus of the hard A and A' blocks independently is greater than about 1,000 MPa, and the tensile modulus of the soft B block is less than about 1,000 MPa.

3. The implantable device of claim 1, wherein the weight fraction of the A and A' blocks is from about 1% to about 99% of the triblock copolymer.

4. The implantable device of claim 1, wherein the A, B and A' blocks each independently comprise a polymer comprising from one to four different types of monomer, wherein each type of monomer has from about 5 to about 5,000 monomer units.

5. The implantable device of claim 1, wherein the A and A' blocks are the same.

6. The implantable device of claim 1, wherein the A and A' blocks are different.

7. The implantable device of claim 1, wherein the B block is immiscible with the A and A' blocks.

8. The implantable device of claim 1, further comprising at least one dihydroxyaryl group conjugated to the polymer ends of the triblock copolymer.

9. The implantable device of claim 8, wherein the at least one dihydroxyaryl group contains a 3,4-dihydroxyphenyl moiety.

10. The implantable device of claim 1, further comprising at least one biocompatible moiety.

11. The implantable device of claim 10, wherein the at least one biocompatible moiety is selected from the group consisting of poly(ethylene oxide), polypropylene glycol), poly(tetramethylene glycol), poly(ethylene oxide-co-propylene oxide), ε-caprolactone, β-butyrolactone, δ-valerolactone, glycolide, poly(N-vinyl pyrrolidone), poly(acrylamide methyl propane sulfonic acid) and salts thereof, poly(styrene sulfonate), sulfonated dextran, polyphosphazenes, poly(orthoesters), poly(tyrosine carbonate), sialic acid, hyaluronic acid or derivatives thereof, copolymers of poly(ethylene glycol) with hyaluronic acid or derivatives thereof, heparin, copolymers of polyethylene glycol with heparin, a graft copolymer of poly(L-lysine) and poly(ethylene glycol), and copolymers thereof.

12. The implantable device of claim 1, further comprising at least one additional biologically absorbable polymer.

13. The implantable device of claim 12, wherein the at least one additional biologically absorbable polymer is selected from the group consisting of poly(hydroxybutyrate), poly(hydroxyvalerate), poly(hydroxybutyrate-co-valerate), poly(caprolactone), poly(lactide-co-glycolide), poly(ethylene-glycol)-block-poly(butyleneterephthalate), poly(ethylene-glycol)-block-poly(butylene terephthalate)-block-poly(ethylene-glycol), poly(butyleneterephthalate)-block-poly(ethylene-glycol)-block poly(butyleneterephthalate), poly(ethylene-glycol)-block-poly(caprolactone), poly(ethylene-glycol)-block-poly(caprolactone)-block-poly(ethylene-glycol), poly(caprolactone)-block-poly(ethylene-glycol)-block-poly(caprolactone), and blends thereof.

14. The implantable device of claim 1, further comprising at least one biologically active agent selected from the group consisting of antiproliferative, antineoplastic, antimitotic, anti-inflammatory, antiplatelet, anticoagulant, antifibrin, antithrombin, antibiotic, antiallergic and antioxidant substances.

15. The implantable device of claim 14, wherein the at least one biologically active agent is selected from the group consisting of paclitaxel, docetaxel, estradiol, nitric oxide donors, super oxide dismutases, super oxide dismutase mimics, 4-amino-2,2,6,6-tetramethylpiperidine-1-oxyl (4-amino-TEMPO), tacrolimus, dexamethasone, rapamycin, rapamycin derivatives, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, progenitor cell-capturing antibodies, prohealing drugs, prodrugs thereof, co-drugs thereof, and combinations thereof.

16. The implantable device of claim 1, wherein the coating is of a thickness of ≤about 10 micron and loses about 100% of its mass within about 12 months.

17. The implantable device of claim 1, which is a stent.

18. The implantable device of claim 14, which is a stent.

19. The implantable device of claim 15, which is a stent.

20. A method of treating a patient in need of treatment of a disorder, the method comprising implanting in the patient the implantable medical device of claim 1, wherein the disorder is selected from the group consisting of atherosclerosis, thrombosis, restenosis, hemorrhage, vascular dissection, vascular perforation, vascular aneurysm, vulnerable plaque, chronic total occlusion, patent foramen *ovale*, claudication, anastomotic proliferation of vein and artificial grafts, bile duct obstruction, ureter obstruction, tumor obstruction, and combinations thereof.

21. A method of treating a patient in need of treatment of a disorder, the method comprising implanting in the patient the implantable medical device of claim 14, wherein the disorder is selected from the group consisting of atherosclerosis, thrombosis, restenosis, hemorrhage, vascular dissection, vascular perforation, vascular aneurysm, vulnerable plaque, chronic total occlusion, patent foramen ovale, claudication, anastomotic proliferation of vein and artificial grafts, bile duct obstruction, ureter obstruction, tumor obstruction, and combinations thereof.

22. The implantable device of claim 14, wherein the at least one biologically active agent is selected from the group consisting of paclitaxel, docetaxel, estradiol, 4-amino-2,2,6,6-tetramethylpiperidine-1-oxyl (4-amino-TEMPO), tacrolimus, dexamethasone, rapamycin, 40-O-(2-hydroxy)ethyl-rapamycin (everolimus), 40-O-(2-ethoxy)ethyl-rapamycin (biolimus), 40-O-(3-hydroxy)propyl-rapamycin, 40-O-[2-(2-hydroxy)ethoxy]ethyl-rapamycin, 40-O-tetrazole-rapamycin, 40-epi-(N1-tetrazolyl)-rapamycin (zotarolimus), pimecrolimus, imatinib mesylate, midostaurin, clobetasol, and combinations thereof.

* * * * *